United States Patent
Sharma et al.

(10) Patent No.: US 7,342,089 B2
(45) Date of Patent: *Mar. 11, 2008

(54) CYCLIC PEPTIDES FOR TREATMENT FOR CACHEXIA

(75) Inventors: Shubh D. Sharma, Cranbury, NJ (US); Ramesh Rajpurohit, Hillsboro, NJ (US); Annette M. Shadiack, Somerset, NJ (US); Yi-Qun Shi, East Brunswick, NJ (US); Kevin D. Burris, Washington Crossing, PA (US)

(73) Assignee: Palatin Technologies, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/174,845

(22) Filed: Jul. 5, 2005

(65) Prior Publication Data

US 2006/0014676 A1 Jan. 19, 2006

Related U.S. Application Data

(63) Continuation-in-part of application No. 10/638,071, filed on Aug. 8, 2003, now Pat. No. 7,176,279, which is a continuation-in-part of application No. PCT/US02/22196, filed on Jul. 11, 2002.

(51) Int. Cl.
*A61K 38/00* (2006.01)
*A61K 38/12* (2006.01)
*C07K 7/00* (2006.01)

(52) U.S. Cl. ............... 530/312; 530/317; 530/321; 530/300; 530/328; 530/329; 514/9; 514/11; 514/12; 514/15; 514/16; 514/18; 424/9.1; 436/811

(58) Field of Classification Search ............... 530/312, 530/317, 321, 300, 328, 329; 514/9, 11, 514/12, 15, 16, 18; 424/9.1; 436/811
See application file for complete search history.

(56) References Cited

U.S. PATENT DOCUMENTS

| | | | |
|---|---|---|---|
| 4,938,763 | A | 7/1990 | Dunn et al. |
| 5,693,608 | A | 12/1997 | Bechgaard et al. |
| 5,731,408 | A | 3/1998 | Hadley et al. |
| 5,908,609 | A | 6/1999 | Lee et al. |
| 5,908,825 | A | 6/1999 | Fasano et al. |
| 5,977,070 | A | 11/1999 | Piazza et al. |
| 6,054,556 | A | 4/2000 | Huby et al. |
| 6,100,048 | A | 8/2000 | Cone et al. |
| 6,284,729 | B1 | 9/2001 | Bernfield et al. |
| 6,432,438 | B1 | 8/2002 | Shukla |
| 6,476,187 | B1 | 11/2002 | Cone et al. |
| 6,613,874 | B1 | 9/2003 | Mazur et al. |
| 6,673,767 | B1 | 1/2004 | Brodbeck et al. |
| 6,693,165 | B2 | 2/2004 | Bednarek |
| 6,716,810 | B1 | 4/2004 | Brennan et al. |
| 2002/0016291 | A1 | 2/2002 | Bednarek |
| 2003/0032791 | A1 | 2/2003 | Alan et al. |
| 2003/0105024 | A1 | 6/2003 | Cone et al. |
| 2003/0113263 | A1 | 6/2003 | Marks et al. |

FOREIGN PATENT DOCUMENTS

WO   WO 03/006620   1/2003

OTHER PUBLICATIONS

Hruby et al. , J. Med. Chem. 38, 3454-3461 (1995).*
Huszar D., Lynch C. A., Fairchild-Huntress V., et al. Targeted disruption of the melanocortin-4 receptor results in obesity in mice. Cell 88:131-141 (1997).
Roubenoff R. The pathophysiology of wasting in the elderly. J. Nutr. 129(1S Suppl.):256S-259S (1999).
Fan W., Boston B. A., Kesterson R.A ., Hruby V. J., Cone R. D. Role of melanocortinergic neurons in feeding and the agouti obesity syndrome. Nature 385:165-168 (1997).
Rossi, M., et al., A C-terminal fragment of Agouti-related protein increases feeding and antagonizes the effect of alpha-melanocyte . . . Endocrinology 139:4428-31 (1998).
Wisse, B.E., et al., Reversal of cancer anorexia by blockade of central melanocortin receptors in rats. Endocrinology 142:3292-3301 (2001).

(Continued)

*Primary Examiner*—Chih-Min Kam
(74) *Attorney, Agent, or Firm*—Stephen A. Slusher

(57) ABSTRACT

A highly selective melanocortin-4 receptor antagonist cyclic peptide of the formula

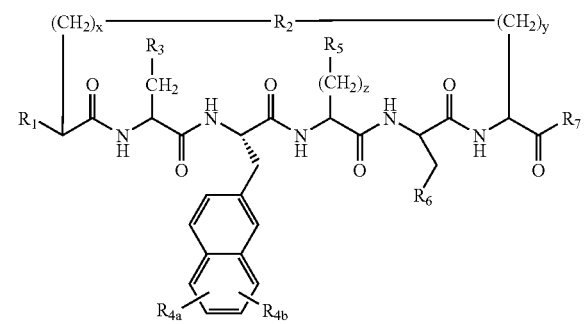

where $R_1$, $R_2$, $R_3$, $R_{4a}$, $R_{4b}$, $R_5$, $R_6$, $R_7$, x, y and z are as defined in the specification, and a method of treating body weight disorders, including cachexia, sarcopenia and wasting syndrome or disease, and treating inflammation and immune disorders.

18 Claims, 1 Drawing Sheet

OTHER PUBLICATIONS

Marks D. L., Ling N., Cone R. D. Role of the central melancortin system in cachexia. Cancer Research 61:1432-1438 (2001).

Synthetic Peptides: A User's Guide, G. A. Grant, editor, W.H. Freeman & Co., New York (1992)—the teachings of which are incorporated herein by reference, including the text and table set forth at pp. 11 through 24.

Hruby V. J., Al obeidi F., Kazmierski W., Biochem. J. 268:249-262 (1990).

Toniolo C., Int. J. Peptide Protein Res. 35:287-300 (1990).

Barn D.R., Morphy J.R., Rees D.C. Synthesis of an array of amides by aluminum chloride assisted cleavage of resin-bound esters. Tetrahedron Lett. 37, 3213-3216 (1996).

DeGrado W. F. Kaiser E. T. Solid-phase synthesis of protected peptides on a polymer bound oxime: Preparation of segments comprising the sequences of a cytotoxic 26-peptide analogue. J. Org. Chem. 47:3258-3261 (1982).

Catania A. et al., Trends Endocrinol. Metab. 11:304-308 (2000).

Gantz I. and Fong T. M., Am. J. Physiol. Endocrinol. Metab. 284:E468-E474 (2003).

Catania A., Gatti S., Colombo G., Lipton J. M., Pharmacol. Rev. 56:1-29 (2004).

Seeley R.J., Blake K., Rushing P.A. et al. The role of CNS glucagons-like peptide-1 (7-36) amide receptors in mediating the visceral illness effects of lithium chloride.J. Neurosci. 20:1616-1621 (2000).

Galande A. K., Spatola A. F. Lett. Pept. Sci. 8:247 (2002).

\* cited by examiner

```
SEQUENCE LISTING

<160> NUMBER OF SEQ ID NOS: 2

<210> SEQ ID NO 1
<211> LENGTH: 4
<212> TYPE: PRT
<213> ORGANISM: Artificial
<220> FEATURE:
<223> OTHER INFORMATION: Core alpha-melanocyte stimulating hormone
      messenger sequence

<400> SEQUENCE: 1

His Phe Arg Trp
1

<210> SEQ ID NO 2
<211> LENGTH: 50
<212> TYPE: PRT
<213> ORGANISM: Homo sapiens

<400> SEQUENCE: 2

Ser Ser Arg Arg Cys Val Arg Leu His Glu Ser Cys Leu Gly Gln Gln
1               5                   10                  15

Val Pro Cys Cys Asp Pro Cys Ala Thr Cys Tyr Cys Arg Phe Phe Asn
            20                  25                  30

Ala Phe Cys Tyr Cys Arg Lys Leu Gly Thr Ala Met Asn Pro Cys Ser
        35                  40                  45

Arg Thr
    50
```

CYCLIC PEPTIDES FOR TREATMENT FOR CACHEXIA

CROSS-REFERENCE TO RELATED APPLICATIONS

This application is a continuation-in-part application of U.S. patent application Ser. No. 10/638,071, filed Aug. 8, 2003, and issued as U.S. Pat. No. 7,176,279 on Feb. 13, 2007, entitled "Cyclic Peptide Compositions and Methods for Treatment of Sexual Dysfunction", to Shubh D. Sharma, et al., which is a continuation-in-part of International Application No. PCT/US02/22196, International Publication No. WO 03/006620, filed on Jul. 11, 2002, entitled "Linear and Cyclic Melanocortin Receptor-Specific Peptides", to Shubh D. Sharma, et al., and the specification and claims thereof of each are incorporated herein by reference.

BACKGROUND OF THE INVENTION

1. Field of the Invention (Technical Field)

The present invention relates to cyclic peptides that are highly-specific antagonists for the melanocortin-4 receptor (MC4-R), and which may be used in the treatment of a variety of body weight disorders including cachexia, sarcopenia and wasting syndrome or disease, and for treatment of inflammation and immune disorders.

2. Description of Related Art

Note that the following discussion refers to a number of publications by author(s) and year of publication, and that due to recent publication dates certain publications are not to be considered as prior art vis-a-vis the present invention. Discussion of such publications herein is given for more complete background and is not to be construed as an admission that such publications are prior art for patentability determination purposes.

Melanocortin Receptors. A family of melanocortin receptor types and subtypes have been identified, including melanocortin-1 receptors (MC1-R) expressed on normal human melanocytes and melanoma cells, melanocortin-2 receptors (MC2-R) for ACTH (adrenocorticotropin) expressed in cells of the adrenal gland, melanocortin-3 and melanocortin-4 receptors (MC3-R and MC4-R) expressed primarily in cells in the hypothalamus, mid-brain and brainstem, and melanocortin-5 receptors (MC5-R), expressed in a wide distribution of peripheral tissues.

Significant work has been done in determining the structure of melanocortin receptors, including both the nucleic acid sequences encoding for the receptors and the amino acid sequences constituting the receptors. MC4-R is a G protein-coupled, 7-transmembrane receptor that is believed to be expressed primarily in the brain. Inactivation of this receptor by gene targeting has been reported to result in mice with the maturity-onset obesity syndrome that is associated with hyperphagia, hyperinsulinemia, and hyperglycemia (Huszar D., Lynch C. A., Fairchild-Huntress V., et al. Targeted disruption of the melanocortin-4 receptor results in obesity in mice. *Cell* 88:131-141 (1997)). MC4-R is a molecular target for therapeutic intervention in energy homeostasis.

In general, compounds specific for MC4-R, and secondarily compounds specific for MC3-R or MC5-R, are believed to be useful in regulation of mammalian energy homeostasis, including use as agents for attenuating food intake and body weight gain. MC4-R antagonists are believed to be useful for weight gain aid, such as for use in treatment of cachexia, sarcopenia, wasting syndrome or disease, and anorexia. MC4-R agonists, by contrast, are believed to be useful for decreasing food intake and body weight gain, such as for treatment of obesity. Compounds that are antagonists specific for MC3-R and MC4-R are additionally believed to be useful in regulating blood pressure, heart rate and other neurophysiologic parameters.

Cachexia and Other Wasting Diseases. Body weight disorders include one or more "wasting" disorders (e.g., wasting syndrome, cachexia, sarcopenia) which cause undesirable and unhealthy loss of weight or loss of body cell mass. In the elderly as well as in cancer and AIDS patients, wasting diseases can result in undesired loss of body weight, including both the fat and the fat-free compartments. Wasting diseases can be the result of inadequate intake of food and/or metabolic changes related to illness and/or the aging process. Cancer patients and AIDS patients, as well as patients following extensive surgery or having chronic infections, immunologic diseases, hyperthyroidism, Crohn's disease, psychogenic disease, chronic heart failure or other severe trauma, frequently suffer from wasting disease. Wasting disease is sometimes also referred to as cachexia, and is generally recognized as a metabolic and, sometimes, an eating disorder. Cachexia may additionally be characterized by hypermetabolism and hypercatabolism. Although cachexia and wasting disease are frequently used interchangeably to refer to wasting conditions, there is at least one body of research which differentiates cachexia from wasting syndrome as a loss of fat-free mass, and particularly, body cell mass (Roubenoff R. The pathophysiology of wasting in the elderly. *J. Nutr.* 129(1 S Suppl.):256S-259S (1999)). Sarcopenia, yet another such disorder which can affect the aging individual, is typically characterized by loss of muscle mass. End stage wasting disease as described above can develop in individuals suffering from either cachexia or sarcopenia.

Melanocortin Antagonist Peptides. Antagonist peptides are based on modifications of the alpha-melanocyte stimulating hormone (α-MSH) core sequence, His-Phe-Arg-Trp (SEQ ID NO:1), and generally include a D-amino acid at the Phe position, most commonly a D-amino acid with a 1- or 2-naphthyl ring or phenyl ring, which may optionally be a substituted ring. Thus U.S. Pat. No. 5,731,408 discloses cyclic lactam heptapeptides that are non-specific antagonists for melanocortin receptors MC3-R and MC4-R, and contain either D-Phe(4-I) or D-Nal 2 in place of the Phe residue. Of particular note is a peptide commonly called SHU9119 (Ac-Nle-cyclo(-Asp-His-D-Nal 2-Arg-Trp-Lys)-NH$_2$) disclosed in U.S. Pat. No. 5,731,408. SHU9119 has been extensively used in research as a reference non-specific melanocortin antagonist. Related cyclic lactam heptapeptides are disclosed in U.S. Pat. No. 6,054,556 which are antagonists for melanocortin receptors MC1-R, MC3-R, MC4-R and MC5-R. These peptides all contain an optionally substituted D-Phe or D-Nal 2 in place of the Phe residue. All of the peptides disclosed in U.S. Pat. Nos. 5,731,408 and 6,054,556 have a C-terminus NH$_2$ group, which is conventional for melanocortin-specific peptides.

Other patents teach the use of melanocortin antagonists for treatment of cachexia and other weight-related disorders. See, for example, U.S. Pat. Nos. 6,716,810; 6,699,873; 6,693,165; 6,613,874; 6,476,187; 6,284,729; 6,100,048; and 5,908,609. However, none of these disclose the peptides of the present invention. U.S. Pat. No. 6,693,165 discloses cyclic heptapeptides and hexapeptides that are asserted to be selective MC4-R antagonists. These peptides all include a D-amino acid containing an optionally substituted 1- or 2-naphthyl, 3-benzothienyl or phenyl in place of the Phe residue in the His-Phe-Arg-Trp (SEQ ID NO:1) core sequence. However, the peptides disclosed in U.S. Pat. No. 6,693,165 optionally omit the His in the His-Phe-Arg-Trp (SEQ ID NO:1) sequence, and when the His position is present, it is limited to Lys or His. Each of the peptides disclosed in U.S. Pat. No. 6,693,165, and the generic formulas given therein, have a C-terminus $NH_2$ group.

Published U.S. Application 2003/0113263, "Methods and Reagents for Using Mammalian Melanocortin Receptor Antagonists to Treat Cachexia", discloses a method for characterizing a compound useful for treating an animal with cachexia, including use of an MC4-R antagonist to treat an animal with cachexia, and specifically disclosing SHU9119. Published U.S. Application 2003/0105024, "Methods and Reagents for Discovering and Using Mammalian Melanocortin Receptor Agonists and Antagonists to Modulate Feeding Behavior in Animals", discloses SHU9119 as a MC receptor antagonist used experimentally to stimulate feeding behavior. U.S. Pat. No. 6,476,187, "Methods and Reagents for Discovering and Using Mammalian Melanocortin Receptor Agonists and Antagonists to Modulate Feeding Behavior in Animals", similarly discloses SHU9119 as a MC receptor antagonist used experimentally to stimulate feeding behavior. Published U.S. Application 2003/0032791, "Novel Melanocortin-4 Receptor Sequences and Screening Assays to Identify Compounds Useful in Regulating Animal Appetite and Metabolic Rate", discloses the experimental use of SHU9119 in various assays. Published U.S. Application 2002/0016291, "Cyclic Peptides as Potent and Selective Melanocortin-4 Receptor Antagonists", discloses SHU9119 as an antagonist at the MC3 and MC4 receptors. In 1977, it was disclosed that SHU9119 enhanced feeding behavior. Fan W., Boston B. A., Kesterson R. A., Hruby V. J., Cone R. D. Role of melanocortinergic neurons in feeding and the agouti obesity syndrome. *Nature* 385: 165-168 (1997); see also Rossi M., Kim M. S., Morgan D. G., et al. A C-terminal fragment of Agouti-related protein increases feeding and antagonizes the effect of alpha-melanocyte stimulating hormone in vivo. *Endocrinology* 139: 4428-31 (1998); Wisse B. E., Frayo R. S., Schwartz M. W., Cummings D. E. Reversal of cancer anorexia by blockade of central melanocortin receptors in rats. *Endocrinology* 142: 3292-3301 (2001); Marks D. L., Ling N., Cone R. D. Role of the central melanocortin system in cachexia. *Cancer Research* 61:1432-1438 (2001).

There remains a significant need for ligands with high specificity for discrete melanocortin receptors, and specifically MC4-R, as well as ligands that are antagonists, or optionally inverse agonists, of MC4-R. In order to reduce unintended pharmacological responses, it is desirable that the ligand be highly specific for the target MC receptor, such as MC4-R. Thus it is desirable that the binding affinity of a ligand for MC4-R be higher, such as at least about ten times higher, for MC4-R than for other MC receptors. High affinity peptide ligands of melanocortin receptors can be used to exploit varied physiological responses associated with the melanocortin receptors, either as antagonists or inverse agonists. For example, antagonists or inverse agonists of MC4-R can be used to treat eating disorders, wasting diseases and cachexia. In addition, melanocortin receptors have an effect on the activity of various cytokines, and high affinity peptide ligands of melanocortin receptors can be used to regulate cytokine activity. Thus such peptide ligands may further be used for treatment of inflammation and other immune disorders.

BRIEF SUMMARY OF THE INVENTION

The invention provides a cyclic peptide of the structural formula:

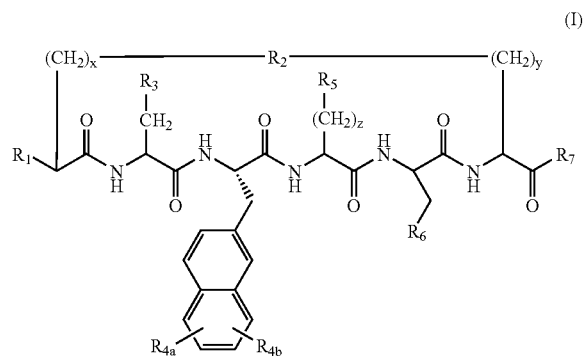

(I)

wherein:

$R_1$ is H, $NH_2$,

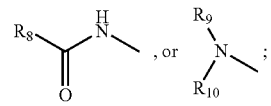

$R_2$ is —C(=O)—NH—, —NH—C(=O)—, —S—, or —S—S—;

$R_3$ is 4-imidazolyl or 3-indolyl;

$R_{4a}$ and $R_{4b}$ are each optional ring substituents, and when one or both are present, are the same or different and independently hydroxyl, halogen, alkyl, or aryl groups attached directly or through an ether linkage;

$R_5$ is —$NH_2$ or —NH(C=NH)$NH_2$;

$R_6$ is 1- or 2-naphthyl or 3-indolyl, optionally with one or two ring substituents, and when one or both ring substitutents are present, are the same or different and independently hydroxyl, halogen, alkyl, or aryl groups attached directly or through an ether linkage;

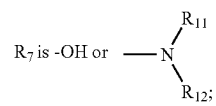

$R_8$ is H, $NH_2$, a lower aliphatic $C_1$ to $C_4$ linear or branched alkyl chain, a $C_1$ to $C_4$ aralkyl, or a $C_1$ to $C_4$ omega amino derivative;

$R_9$ is H, a lower aliphatic $C_1$ to $C_4$ linear or branched alkyl chain, a $C_1$ to $C_4$ aralkyl, or a $C_1$ to $C_4$ omega amino derivative;

$R_{10}$ is an aliphatic L- or D-amino acid, an N-acylated L- or D-amino acid or a linear or branched $C_1$ to $C_{17}$ alkyl, aryl, heteroaryl, alkene, alkenyl, or aralkyl chain;

$R_{11}$ and $R_{12}$ are each independently H or a $C_1$ to $C_4$ linear or branched alkyl chain, on the proviso that both $R_{11}$ and $R_{12}$ are not H;

x is 1 to 4, and y is 1 to 5, provided that x+y is 2 to 7; and z is 2 to 5.

In one embodiment, the cyclic peptide has the structural formula:

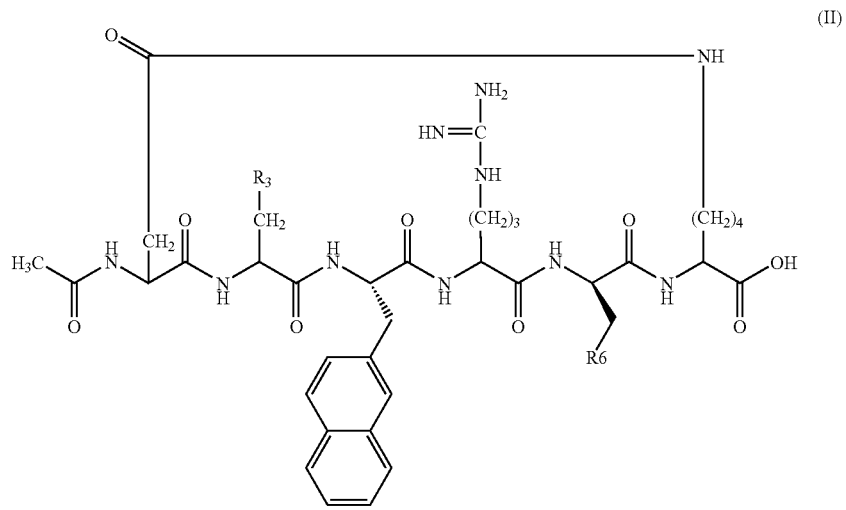
(II)

wherein $R_3$ and $R_6$ are as defined for the peptide of structural formula (I). Representative cyclic peptides of formula (II) include:

Ac-cyclo(-Asp-His-D-Nal 2-Arg-Trp-Lys)-OH;
Ac-cyclo(-Asp-His-D-Nal 2-Arg-Nal 2-Lys)-OH; or
Ac-cyclo(-Asp-Trp-D-Nal 2-Arg-Nal 2-Lys)-OH.

In another embodiment, the cyclic peptide has the structural formula:

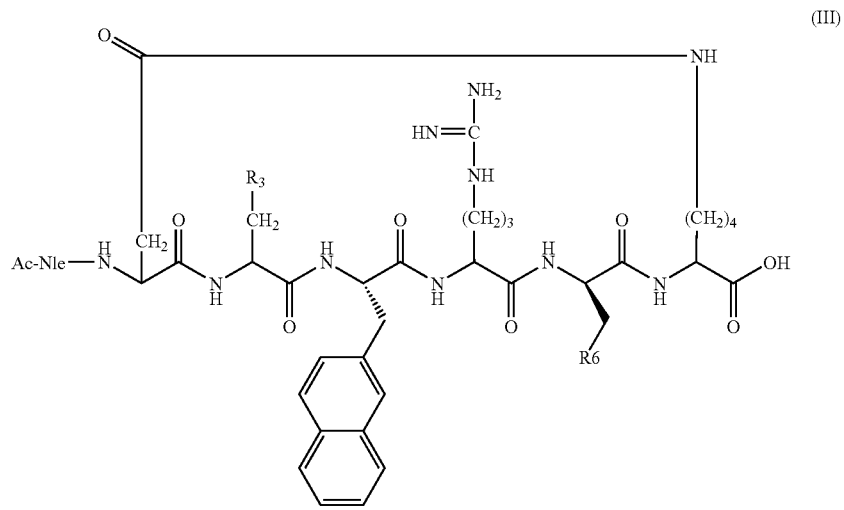
(III)

wherein $R_3$ and $R_6$ are as defined for the peptide of structural formula (I). Representative cyclic peptides of formula (III) include:

Ac-Nle-cyclo(-Asp-His-D-Nal 2-Arg-Trp-Lys)-OH;
Ac-Nle-cyclo(-Asp-His-D-Nal 2-Arg-Nal 2-Lys)-OH; or
Ac-Nle-cyclo(-Asp-Trp-D-Nal 2-Arg-Nal 2-Lys)-OH.

In another embodiment, the cyclic peptide has the structural formula:

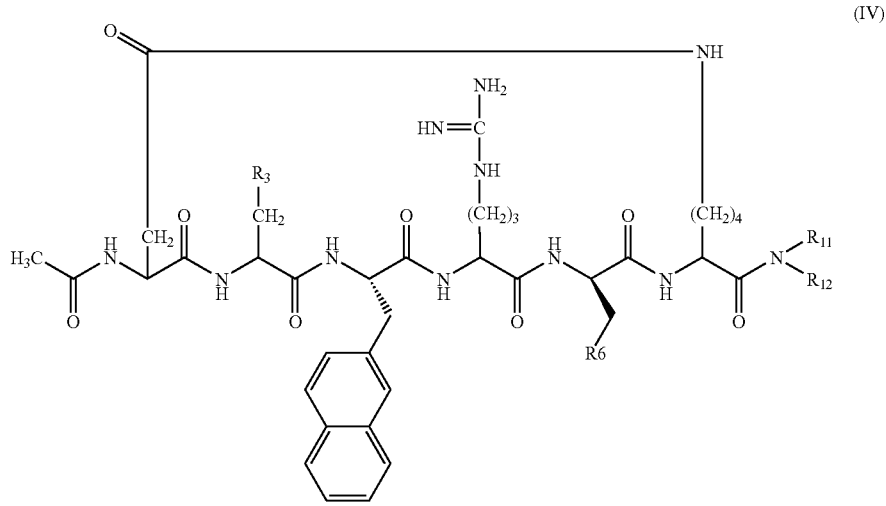

(IV)

wherein $R_3$, $R_6$, $R_{11}$ and $R_{12}$ are as defined for the peptide of structural formula (I). Representative cyclic peptides of formula (IV) include:

Ac-cyclo(-Asp-Trp-D-Nal 2-Arg-Nal 2-Lys)-NH—CH$_2$—CH$_3$;
Ac-cyclo(-Asp-Trp-D-Nal 2-Arg-Nal 2-Lys)-N(CH$_3$)$_2$; or
Ac-cyclo(-Asp-Trp-D-Nal 2-Arg-Nal 2-Lys)-NH—CH$_3$.

In another embodiment, the cyclic peptide has the structural formula:

wherein $R_3$, $R_5$, $R_6$, $R_{11}$, $R_{12}$ and z are as defined for the peptide of structural formula (I). Representative cyclic peptides of formula (V) include:

H-cyclo(-Asp-Trp-D-Nal 2-Arg-Nal 2-Lys)-NH—CH$_2$—CH$_3$;
H-cyclo(-Asp-Trp-D-Nal 2-Arg-Nal 2-Lys)-NH—CH$_3$;
H-cyclo(-Asp-Trp-D-Nal 2-Arg-Nal 2-Lys)-N(CH$_3$)$_2$;
H-cyclo(-Asp-Trp-D-Nal 2-Lys-Nal 2-Lys)-NH—CH$_2$—CH$_3$;
H-cyclo(-Asp-Trp-D-Nal 2-Lys-Nal 2-Lys)-NH—CH$_3$; or
H-cyclo(-Asp-Trp-D-Nal 2-Lys-Nal 2-Lys)-N(CH$_3$)$_2$.

Another embodiment of the present invention further provides a pharmaceutical preparation, comprising a cyclic peptide of any of formulas (I) to (V) or a pharmaceutically acceptable salt thereof, and a pharmaceutically acceptable carrier.

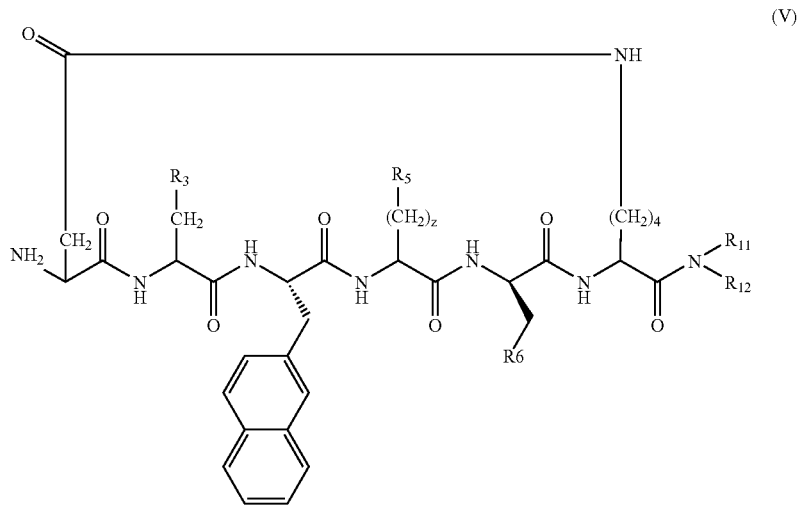

(V)

Yet another embodiment of the present invention provides a method of treating cachexia. The method includes administration of a pharmaceutically sufficient amount of a pharmaceutical preparation as provided. Yet another embodiment of the present invention provides a method of treating inflammation and immune-mediated disorders. The method includes administration of a pharmaceutically sufficient amount of a pharmaceutical preparation as provided.

In yet another embodiment, the invention provides a cyclic hexapeptide with a C-terminus hydroxyl or N-alkyl group, wherein the N-alkyl group comprises one or two $C_1$ to $C_4$ linear or branched alkyl chains, the hexapeptide containing the core sequence His-D-Nal 2-X—Y or Trp-D-Nal 2-X—Y, wherein X is an L-amino acid selected from the group consisting of Arg, Lys, Orn, Harg and Hlys and Y is an L- or D-amino acid selected from the group consisting of Nal 1, Nal 2 and Trp, and wherein any aromatic ring in the core sequence may optionally include one or two ring substituents, and when one or both ring substitutents are present, are the same or different and independently hydroxyl, halogen, alkyl, or aryl groups attached directly or through an ether linkage. In one embodiment, the cyclic hexapeptide has an N-terminus Ac or $NH_2$ group. The cyclic hexapeptide may be cyclized by formation of an amide bond between an amino group of a side chain of an amino acid in the 1 position or an amino group of the N-terminus group of the amino acid in the 1 position and a side chain carboxyl group of an amino acid residue at the 6 position. Alternatively, the cyclic hexapeptide may be cyclized by formation of an amide bond between a side chain carboxyl group of an amino acid residue in the 1 position and an amino group of a side chain of an amino acid at the 6 position. In yet another alternative, the cyclic hexapeptide may be cyclized by formation of a covalent bond comprising an amide, disulfide, thioether, Schiff base, reduced Schiff base, imide, secondary amine, carbonyl, urea, hydrazone or oxime bond. In a preferred embodiment of the cyclic hexapeptide, the core sequence is in the 2 to 5 positions and is His-D-Nal 2-X-Nal 2, and is cyclized through the amino acids in the 1 and 6 positions. In another preferred embodiment of the cyclic hexapeptide the core sequence is in the 2 to 5 positions and is Trp-D-Nal 2-X-Nal 2, and is cyclized through the amino acids in the 1 and 6 positions. In yet another preferred embodiment of the cyclic hexapeptide the core sequence is in the 2 to 5 positions and is His-D-Nal 2-X-Trp, and is cyclized through the amino acids in the 1 and 6 positions. Positions are determined in the conventional manner, by counting amino acid residue positions from the N-terminus to the C-terminus.

An object of the present invention is to provide a peptide-based melanocortin receptor-specific pharmaceutical, wherein the peptide is a highly-selective MC4-R antagonist or inverse agonist, for use in treatment of cachexia.

Another object of the present invention is to provide a peptide-based melanocortin receptor-specific pharmaceutical for use in treatment of cachexia wherein the peptide has a C-terminus hydroxyl.

Another object of the invention is to provide a peptide-based melanocortin receptor-specific pharmaceutical for use in treatment of cachexia wherein the peptide has a C-terminus N-alkyl group.

Another object of this invention is to provide peptides which are highly specific for melanocortin receptor MC4-R and which are antagonists or inverse agonists.

Another object of the present invention is a peptide-based melanocortin receptor-specific pharmaceutical for use in treatment of inflammation and other immune related disorders.

Yet another object of the present invention is to provide a melanocortin receptor-specific pharmaceutical for use in treatment wherein administration of the treatment is via nasal administration.

According to one embodiment of the present invention, there is provided a C-terminus hydroxyl cyclic peptide that is a highly specific MC4-R antagonist or inverse agonist suitable for-use as a specific pharmaceutical in treatment of eating disorders and which is efficacious at low doses.

Another embodiment of the present invention provides a C-terminus N-alkyl cyclic peptide that is a highly specific MC4-R antagonist or inverse agonist suitable for use as a specific pharmaceutical in treatment of eating disorders and which is efficacious at low doses.

Another aspect of the present invention provides a highly specific MC4-R cyclic peptide antagonist or inverse agonist that is effective over a significant dose range.

Yet another aspect of the present invention provides highly specific MC4-R cyclic peptide antagonists or inverse agonists for use in treatment of eating disorders which, because of increased efficacy at low doses, may be administered by delivery systems other than art conventional intravenous, subcutaneous or intramuscular injection, including but not limited to oral delivery systems, nasal delivery systems and mucous membrane delivery systems.

Other objects, advantages and novel features, and further scope of applicability of the present invention will be set forth in part in the detailed description to follow, taken in conjunction with the accompanying drawings, and in part will become apparent to those skilled in the art upon examination of the following, or may be learned by practice of the invention. The objects and advantages of the invention may be realized and attained by means of the instrumentalities and combinations particularly pointed out in the appended claims.

BRIEF DESCRIPTION OF THE SEVERAL VIEWS OF THE DRAWINGS

The accompanying drawings, which are incorporated into and form a part of the specification, illustrate one or more embodiments of the present invention and, together with the description, serve to explain the principles of the invention. The drawings are only for the purpose of illustrating one or more preferred embodiments of the invention and are not to be construed as limiting the invention. In the drawings.

DETAILED DESCRIPTION OF THE INVENTION

Definitions

Figure 1:
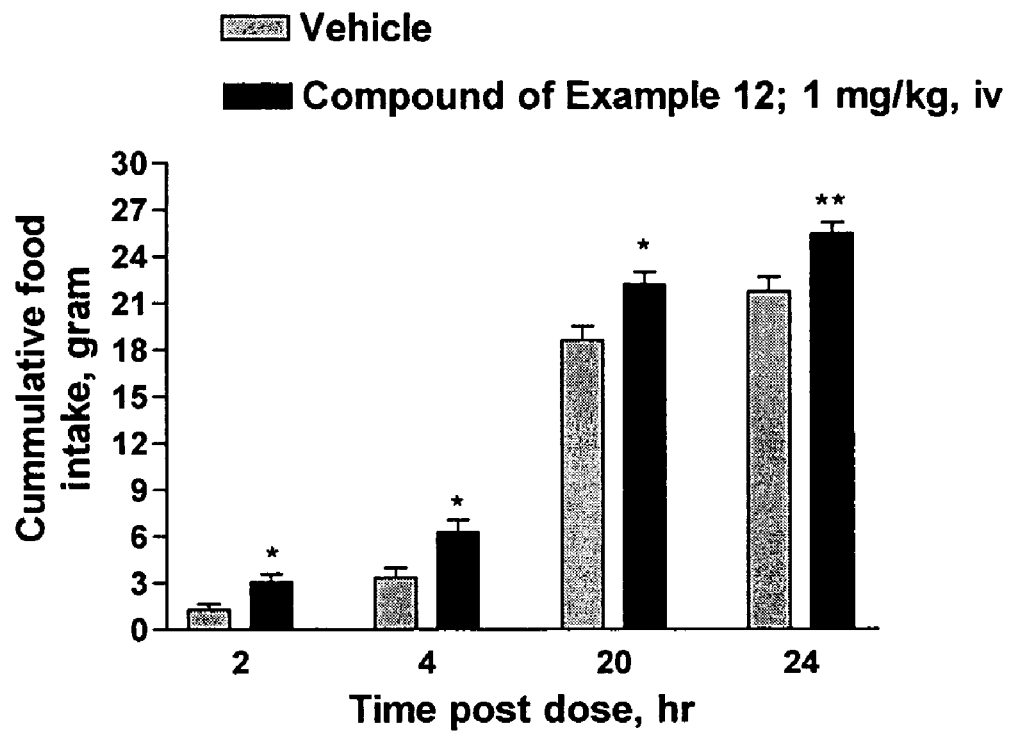
FIG. 1 is a graph of the cumulative 24 hour food intake in male rats, comparing the effect of IV administration of 1 mg/kg of the compound of Example 12 against the same volume of vehicle.

Certain terms as used throughout the specification and claims are defined as follows.

The terms "bind," "binding," "complex," and "complexing," as used throughout the specification and claims, are generally intended to cover all types of physical and chemical binding, reactions, complexing, attraction, chelating and the like.

The "peptides" of this invention can be a) naturally-occurring, b) produced by chemical synthesis, c) produced by recombinant DNA technology, d) produced by biochemical or enzymatic fragmentation of larger molecules, e) produced by methods resulting from a combination of methods a through d listed above, or f) produced by any other means for producing peptides.

By employing chemical synthesis, a preferred means of production, it is possible to introduce various amino acids which do not naturally occur along the chain, modify the N— or C-terminus, and the like, thereby providing for improved stability and formulation, resistance to protease degradation, and the like.

The term "peptide" as used throughout the specification and claims is intended to include any structure comprised of two or more amino acids, including chemical modifications and derivatives of amino acids. The amino acids forming all or a part of a peptide may be naturally occurring amino acids, stereoisomers and modifications of such amino acids, non-protein amino acids, post-translationally modified amino acids, enzymatically modified amino acids, constructs or structures designed to mimic amino acids, and the like, so that the term "peptide" includes pseudopeptides and peptidomimetics, including structures which have a non-peptidic backbone. The term "peptide" also includes dimers or multimers of peptides. A "manufactured" peptide includes a peptide produced by chemical synthesis, recombinant DNA technology, biochemical or enzymatic fragmentation of larger molecules, combinations of the foregoing or, in general, made by any other method.

The term "amino acid side chain moiety" used in this invention, including as used in the specification and claims, includes any side chain of any amino acid, as the term "amino acid" is defined herein. This thus includes the side chain moiety present in naturally occurring amino acids. It further includes side chain moieties in modified naturally occurring amino acids, such as glycosylated amino acids. It further includes side chain moieties in stereoisomers and modifications of naturally occurring protein amino acids, non-protein amino acids, post-translationally modified amino acids, enzymatically synthesized amino acids, derivatized amino acids, constructs or structures designed to mimic amino acids, and the like. For example, the side chain moiety of any amino acid disclosed herein is included within the definition. A "derivative" of an amino acid side chain moiety is included within the definition of an amino acid side chain moiety.

The "derivative" of an amino acid side chain moiety includes any modification to or variation in any amino acid side chain moieties, including a modification of naturally occurring amino acid side chain moieties. By way of example, derivatives of amino acid side chain moieties include straight chain or branched, cyclic or noncyclic, substituted or unsubstituted, saturated or unsaturated, alkyl, aryl or aralkyl moieties.

The "amino acids" used in embodiments of the present invention, and the term as used in the specification and claims, include the known naturally occurring protein amino acids, which are referred to by both their common three letter abbreviation and single letter abbreviation. See generally *Synthetic Peptides: A User's Guide*, G. A. Grant, editor, W. H. Freeman & Co., New York (1992), the teachings of which are incorporated herein by reference, including the text and table set forth at pages 11 through 24. As set forth above, the term "amino acid" also includes stereoisomers and modifications of naturally occurring protein amino acids, non-protein amino acids, post-translationally modified amino acids, enzymatically synthesized amino acids, derivatized amino acids, constructs or structures designed to mimic amino acids, and the like. Modified and unusual amino acids are described generally in *Synthetic Peptides: A User's Guide*, cited above; Hruby V. J., Al-obeidi F., Kazmierski W., *Biochem. J.* 268:249-262 (1990); and Toniolo C., *Int. J. Peptide Protein Res.* 35:287-300 (1990); the teachings of all of which are incorporated herein by reference. In addition, the following abbreviations have the meanings giving:

7'-amino-heptanoyl-NH$_2$—(CH$_2$)$_6$CO—
Harg—Homo arginine
Hlys—Homo lysine
Nal 1—3-(1-naphthyl)alanine
Nal 2—3-(2-naphthyl)alanine In the listing of peptides according to the present invention, conventional amino acid residues have their conventional meaning as given in Chapter 2400 of the *Manual of Patent Examining Procedure*, 8$^{th}$ Ed. Thus, "Nle" is norleucine, "Asp" is aspartic acid, "His" is histidine, "D-Phe" is D-phenylalanine, "Arg" is arginine, "Trp" is tryptophan, "Lys" is lysine, and so on.

The term "alkene" includes unsaturated hydrocarbons that contain one or more double carbon-carbon bonds. Examples of such alkene groups include ethylene, propene, and the like.

The term "alkenyl" includes a linear monovalent hydrocarbon radical of two to six carbon atoms or a branched monovalent hydrocarbon radical of three to six carbon atoms containing at least one double bond; examples thereof include ethenyl, 2-propenyl, and the like.

The "alkyl" groups specified herein include those alkyl radicals of the designated length in either a straight or branched configuration. Examples of such alkyl radicals include methyl, ethyl, propyl, isopropyl, butyl, sec-butyl, tertiary butyl, pentyl, isopentyl, hexyl, isohexyl, and the like.

The term "alkynal" includes a linear monovalent hydrocarbon radical of two to six carbon atoms or a branched monovalent hydrocarbon radical of three to six carbon atoms containing at least one triple bond; examples thereof include ethynyl, propynal, butynyl, and the like.

The term "aryl" includes a monocyclic or bicyclic aromatic hydrocarbon radical of 6 to 12 ring atoms, and optionally substituted independently with one or more substituents selected from alkyl, haloalkyl, cycloalkyl, alkoxy, alkythio, halo, nitro, acyl, cyano, amino, monosubstituted amino, disubstituted amino, hydroxy, carboxy, or alkoxycarbonyl. Examples of an aryl group include phenyl, biphenyl, naphthyl, 1-naphthyl, and 2-naphthyl, derivatives thereof, and the like.

The term "aralkyl" includes a radical —R$^a$R$^b$ where R$^a$ is an alkylene (a bivalent alkyl) group and R$^b$ is an aryl group as defined above. Examples of aralkyl groups include benzyl, phenylethyl, 3-(3-chlorophenyl)-2-methylpentyl, and the like.

The term "aliphatic" includes compounds with hydrocarbon chains, such as for example alkanes, alkenes, alkynes, and derivatives thereof.

The term "acyl" includes a group RCO—, where R is an organic group. An example is the acetyl group CH$_3$CO—, referred to herein as "Ac".

A peptide or aliphatic moiety is "acylated" when an alkyl or substituted alkyl group as defined above is bonded through one or more carbonyl {—(C=O)—} groups. A peptide is most usually acylated at the N-terminus.

An "omega amino derivative" includes an aliphatic moiety with a terminal amino group. Examples of omega amino derivatives include aminoheptanoyl, such as 7'-amino-heptanoyl, and the amino acid side chain moieties of ornithine and lysine.

The term "heteroaryl" includes mono- and bicyclic aromatic rings containing from 1 to 4 heteroatoms selected from nitrogen, oxygen and sulfur. 5- or 6-membered heteroaryl are monocyclic heteroaromatic rings; examples thereof include thiazole, oxazole, thiophene, furan, pyrrole, imidazole, isoxazole, pyrazole, triazole, thiadiazole, tetrazole, oxadiazole, pyridine, pyridazine, pyrimidine, pyrazine, and the like. Bicyclic heteroaromatic rings include, but are not limited to, benzothiadiazole, indole, benzothiophene, benzofuran, benzimidazole, benzisoxazole, benzothiazole, quinoline, benzotriazole, benzoxazole, isoquinoline, purine, furopyridine and thienopyridine.

An "amide" includes compounds that have a trivalent nitrogen attached to a carbonyl group (—CO.NH$_2$), such as for example methylamide, ethylamide, propylamide, and the like.

An "imide" includes compounds containing an imido group (—CO.NH.CO—).

An "amine" includes compounds that contain an amino group (—NH$_2$).

A "nitrile" includes compounds that are carboxylic acid derivatives and contain a (—CN) group bound to an organic group.

The term "halogen" is intended to include the halogen atoms fluorine, chlorine, bromine and iodine, and groups including one or more halogen atoms, such as —CF$_3$ and the like.

The term "composition", as in pharmaceutical composition, is intended to encompass a product comprising the active ingredient(s), and the inert ingredient(s) that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing a cyclic peptide of the present invention and a pharmaceutically acceptable carrier.

A single amino acid, including stereoisomers and modifications of naturally occurring protein amino acids, non-protein amino acids, post-translationally modified amino acids, enzymatically synthesized amino acids, derivatized amino acids, constructs or structures designed to mimic amino acids, and the like, including all of the foregoing, is sometimes referred to herein as a "residue."

By a melanocortin receptor "agonist" is meant a naturally occurring substance or manufactured drug substance or composition that can interact with a melanocortin receptor and initiate a pharmacological response characteristic of the melanocortin receptor. By a melanocortin receptor "antagonist" is meant a naturally occurring substance or manufactured drug substance or composition that opposes the melanocortin receptor-associated responses normally induced by a melanocortin receptor agonist agent. By a melanocortin receptor "inverse agonist" is meant a drug or a compound that stabilizes the inactive conformation of the melanocortin receptor and inhibits basal activity.

"Eating disorders" are those related to underweight, cachexia, anorexia or bulimia of any cause in humans.

"Cachexia" refers to a state of general ill health and malnutrition. It is often associated with and induced by malignant cancer, cystic fibrosis or AIDS, and is characterized by loss of appetite, loss of body mass, especially lean body mass, and muscle wasting.

"Anorexia" refers simply to a loss of appetite, whether brought on by medical, physiological or psychological factors. Anorexia is often closely associated with, and generally contributes to, cachexia seen in patients with advanced cancers and other conditions.

Cyclic Peptides of the Invention

One embodiment of the present invention provides cyclic peptides which include the core sequence His-D-Nal 2-Arg-Nal 2, Trp-D-Nal 2-Arg-Nal 2, His-D-Nal 2-Arg-Trp or homologs or analogs of the foregoing, including peptides with one or more substituted ring groups in the core sequence. In each of the foregoing, Arg may be substituted with Lys. In another embodiment the invention provides cyclic peptides which include the core sequence His-D-Nal 2-Arg-Nal 2, Trp-D-Nal 2-Arg-Nal 2, His-D-Nal 2-Arg-Trp, or homologs or analogs of the foregoing, including substitution of Lys for Arg, in which the peptide is deamidated, which is to say that it does not include an —NH$_2$ group at the C-terminus. In a preferred embodiment, the deamidated α-MSH cyclic peptides of this invention have an —OH group at the C-terminus, and are thus a free acid form of cyclic peptide. In an alternative preferred embodiment, the peptide has a substituted amide, and specifically an N-alkyl group, at the C-terminus.

Another aspect of the present invention provides certain cyclic peptides which are highly specific for a melanocortin receptor, preferably MC4-R, and alternatively for both MC4-R and MC3-R. Most preferably the cyclic peptides bind to MC4-R with high affinity, with a Ki value of at least 100 nM, preferably of at least 10 nM and most preferably from about 0.01 nM to about 2 nM. In some embodiments the cyclic peptides are functionally inverse agonists with respect to such receptor or receptors. However, the peptides of this invention need not be inverse agonists. Such peptides can preferably be employed in the treatment of eating disorders, and may be characterized in part as inducing weight increase in mammals, including but not limited to rodents, canines and humans.

The peptide is a cyclic peptide. A cyclic peptide can be obtained by inducing the formation of a covalent bond between an amino group at the N-terminus of the peptide, if provided, and a carboxyl group at the C-terminus, if provided. A cyclic peptide can also be obtained by forming a covalent bond between a terminal reactive group and a reactive amino acid side chain moiety, or between two reactive amino acid side chain moieties. A cyclic peptide can also be obtained by forming a disulfide covalent bond between two sulfhydryl group containing amino acid side chain moieties or a terminal sulfhydryl group and a sulfhydryl group in another amino acid side chain moiety. Peptides with lanthionine, cystathionine, or penthionine covalent bonds can also be formed, such as cyclic bonds formed from cysteine, homocysteine or penicillamine amino acid residues. These bonds are thioether-bridged bonds. Galande A. K., Spatola A. F. *Lett. Pept. Sci.* 8:247 (2002), disclosing methods of making such bonds, is incorporated herein by reference. Thus a cyclic peptide can also be obtained by forming a thioether covalent bond between two reactive amino acid side chain moieties or between a terminal reactive group and a reactive amino acid side chain moiety.

One skilled in the art would know that the means by which a given peptide is made cyclic is determined by the reactive groups present in the peptide and the desired characteristics of the peptide.

The cyclic peptides as disclosed in the several embodiments of the present invention are characterized, in part, in that the peptides are preferably highly selective for MC4-R. For example, with SHU9119 the ratio of the Ki values for MC4-R to MC3-R is, under the assay conditions employed herein, less than about 1:6, the ratio of MC4-R to MC5-R is less than about 1:3, and the ratio of MC4-R to MC1-R is less than about 1:7. Other researchers (e.g., Schioth H. B. et al. *Peptides* 18:1009-1013(1997)), while reporting different values, concur that SHU9119 is non-selective. It may thus be seen that SHU9119 is not highly selective for MC4-R. By contrast, certain peptides of this invention are significantly more selective. The cyclic peptide of Example 16, Ac-cyclo(-Asp-Trp-D-Nal 2-Arg-Nal 2-Lys)-OH, has, under the same assay conditions, a ratio of Ki values for MC4-R to MC3-R of approximately 1:110, for MC4-R to MC5-R of approximately 1:187, and for MC4-R to MC1-R of approximately 1:12,095. The cyclic peptide of Example 19, Ac-cyclo(-Asp-Trp-D-Nal 2-Arg-Nal 2-Lys)-NH—CH$_3$, has, again under the same assay conditions, a ratio of Ki values for MC4-R to MC3-R of approximately 1:54, for MC4-R to MC5-R of approximately 1:101, and for MC4-R to MC1-R of approximately 1:10,531. It may thus be seen that at all pharmaceutically relevant doses the cyclic peptides of this invention are highly selective for MC4-R.

The cyclic peptides as disclosed in the several embodiments of the invention are further characterized in that they are preferable not agonists for any MC receptor, and are preferably either inactive or antagonists as to all MC receptors other than MC4-R. All cyclic peptides of the invention are functional antagonists as to MC4-R. Certain peptides of the invention are partial agonists or agonists, as to MC1-R; these are peptides with a His-D-Nal 2-Arg-Nal 2, His-D-Nal 2-Arg-Trp, or Trp-D-Nal 2-Arg-Nal 2 core sequence and a C-terminus N-alkyl or hydroxyl. However, these peptides are functional antagonists as to MC3-R and MC4-R.

Peptide Synthesis

The cyclic peptides as disclosed in the several embodiments of this invention may be readily synthesized by any known conventional procedure for the formation of a peptide linkage between amino acids. Such conventional procedures include, for example, any solution phase procedure permitting a condensation between the free alpha amino group of an amino acid residue having its carboxyl group or other reactive groups protected and the free primary carboxyl group of another amino acid residue having its amino group or other reactive groups protected. In a preferred conventional procedure, the cyclic peptides of this invention may be synthesized by solid-phase synthesis and purified according to methods known in the art. Any of a number of well-known procedures utilizing a variety of resins and reagents may be used to prepare the cyclic peptides of this invention.

The process for synthesizing the cyclic peptides may be carried out by a procedure whereby each amino acid in the desired sequence is added one at a time in succession to another amino acid residue or by a procedure whereby peptide fragments with the desired amino acid sequence are first synthesized conventionally and then condensed to provide the desired peptide. The resulting peptide is then cyclized to yield a cyclic peptide of the invention.

Solid phase peptide synthesis methods are well known and practiced in the art. In such methods the synthesis of peptides of the invention can be carried out by sequentially incorporating the desired amino acid residues one at a time into the growing peptide chain according to the general principles of solid phase methods. These methods are disclosed in numerous references, including Merrifield R. B., Solid phase synthesis (Nobel lecture). *Angew. Chem.* 24:799-810 (1985) and Barany et al., *The Peptides, Analysis, Synthesis and Biology*, Vol. 2, Gross E. and Meienhofer J., Eds. Academic Press 1-284 (1980).

In chemical syntheses of peptides, reactive side chain groups of the various amino acid residues are protected with suitable protecting groups, which prevent a chemical reaction from occurring at that site until the protecting group is removed. Also common is the protection of the alpha amino group of an amino acid residue or fragment while that entity reacts at the carboxyl group, followed by the selective removal of the alpha amino protecting group to allow a subsequent reaction to take place at that site. Specific protecting groups have been disclosed and are known in solid phase synthesis methods and solution phase synthesis methods.

Alpha amino groups may be protected by a suitable protecting group, including a urethane-type protecting group, such as benzyloxycarbonyl (Z) and substituted benzyloxycarbonyl, such as p-chlorobenzyloxycarbonyl, p-nitrobenzyloxycarbonyl, p-bromobenzyloxycarbonyl, p-biphenyl-isopropoxycarbonyl, 9-fluorenylmethoxycarbonyl (Fmoc) and p-methoxybenzyloxycarbonyl (Moz); aliphatic urethane-type protecting groups, such as t-butyloxycarbonyl (Boc), diisopropylmethoxycarbonyl, isopropoxycarbonyl, and allyloxycarbonyl. Fmoc is preferred for alpha amino protection.

Guanidino groups may be protected by a suitable protecting group, such as nitro, p-toluenesulfonyl (Tos), Z, pentamethylchromanesulfonyl (Pmc), adamantyloxycarbonyl, pentamethyldihydrobenzofuran-5-sulfonyl (Pbf) and Boc. Pmc is a preferred protecting group for Arg.

The peptides of the invention described herein were prepared using solid phase synthesis, such as by means of a Symphony Multiplex Peptide Synthesizer (Rainin Instrument Company) automated peptide synthesizer, using programming modules as provided by the manufacturer and following the protocols set forth in the manufacturer's manual.

Solid phase synthesis is commenced from the C-terminal end of the peptide by coupling a protected alpha amino acid to a suitable resin. Such starting material is prepared by attaching an alpha amino-protected amino acid by an ester linkage to a p-benzyloxybenzyl alcohol (Wang) resin or a 2-chlorotrityl chloride resin, by an amide bond between an Fmoc-Linker, such as p-[(R,S)-α-[1-(9H-fluor-en-9-yl)-methoxyformamido]-2,4-dimethyloxybenzyl]-phenoxyacetic acid (Rink linker) to a benzhydrylamine (BHA) resin, or by other means well known in the art. Fmoc-Linker-BHA resin supports are commercially available and generally used when feasible. The resins are carried through repetitive cycles as necessary to add amino acids sequentially. The alpha amino Fmoc protecting groups are removed under basic conditions. Piperidine, piperazine, diethylamine, or morpholine (20-40% v/v) in N,N-dimethylformamide (DMF) may be used for this purpose.

Following removal of the alpha amino protecting group, the subsequent protected amino acids are coupled stepwise in the desired order to obtain an intermediate, protected peptide-resin. The activating reagents used for coupling of the amino acids in the solid phase synthesis of the peptides are well known in the art. After the peptide is synthesized, if desired, the orthogonally protected side chain protecting groups may be removed using methods well known in the art for further derivatization of the peptide.

Reactive groups in a peptide can be selectively modified, either during solid phase synthesis or after removal from the resin. For example, peptides can be modified to obtain N-terminus modifications, such as acetylation, while on resin, or may be removed from the resin by use of a cleaving reagent and then modified. Methods for N-terminus modification, such as acetylation, or C-terminus modification, such as introduction of an N-acetyl group, are known in the art. Similarly, methods for modifying side chains of amino acids are well known to those skilled in the art of peptide synthesis. The choice of modifications made to reactive groups present on the peptide will be determined, in part, by the characteristics that are desired in the peptide.

The peptide can, in one embodiment, be cyclized prior to cleavage from the peptide resin. For cyclization through reactive side chain moieties, the desired side chains are deprotected, and the peptide suspended in a suitable solvent and a cyclic coupling agent added. Suitable solvents include, for example DMF, dichloromethane (DCM) or 1-methyl-2-pyrrolidone (NMP). Suitable cyclic coupling reagents include, for example, 2-(1H-benzotriazol-1-yl)-1,1,3,3-tetramethyluronium tetrafluoroborate (TBTU), 2-(1H-benzotriazol-1-yl)-1,1,3,3-tetramethyluronium hexafluorophosphate (HBTU), benzotriazole-1-yl-oxy-tris(dimethylamino)phosphoniumhexafluorophosphate (BOP), benzotriazole-1-yl-oxy-tris(pyrrolidino)phosphoniumhexafluorophosphate (PyBOP), 2-(7-aza-1H-benzotriazol-1-yl)-1,1,3,3-tetramethyluronium tetrafluoroborate (TATU), 2-(2-oxo-1(2H)-pyridyl)-1,1,3,3-tetramethyluronium tetrafluoroborate (TPTU) or N,N'-dicyclohexylcarbodiimide/1-hydroxybenzotriazole (DCCI/HOBt). Coupling is conventionally initiated by use of a suitable base, such as N,N-diisopropylethylamine (DIPEA), sym-collidine or N-methylmorpholine (NMM).

Following cleavage of peptides from the solid phase following their synthesis, the peptide can be purified by any number of methods, such as reverse phase high performance liquid chromatography (RP-HPLC), using a suitable column, such as a $C_{18}$ column. Other methods of separation or purification, such as methods based on the size or charge of the peptide, can also be employed. Once purified, the peptide can be characterized by any number of methods, such as high performance liquid chromatograph (HPLC), amino acid analysis, mass spectrometry, and the like.

Peptides of the present invention with a substituted amide derivative C-terminus, typically an N-alkyl group, are prepared by solid phase synthesis commenced from the C-terminal end of the peptide by coupling a protected alpha amino acid to a suitable resin. Such methods for preparing substituted amide derivatives on solid phase have been described in the art. See, for example, Barn D. R., Morphy J. R., Rees D. C. Synthesis of an array of amides by aluminum chloride assisted cleavage of resin-bound esters. *Tetrahedron Lett.* 37, 3213-3216 (1996); DeGrado W. F. Kaiser E. T. Solid-phase synthesis of protected peptides on a polymer bound oxime: Preparation of segments comprising the sequences of a cytotoxic 26-peptide analogue. *J. Org. Chem.* 47:3258-3261 (1982). Such starting material can be prepared by attaching an alpha amino-protected amino acid by an ester linkage to a p-benzyloxybenzyl alcohol (Wang) resin by well known means. The peptide chain is grown with the desired sequence of amino acids, the peptide cyclized and the peptide-resin treated with a solution of appropriate amine and aluminum choride (such as methyl amine, dimethyl amine, ethylamine, and so on) in dichloromethane. The resulting peptide amide derivative is released in solution from the resin. The resin is filtered and the peptide amide derivative recovered by concentration of solvent followed by precipitation with ether. The crude peptide is dried and remaining amino acid side chain protective groups cleaved using trifluoroacetic acid (TFA) in the presence of water and 1,2-ethanedithiol (EDT). The final product is precipitated by adding cold ether and collected by filtration. Final purification is by RP-HPLC using a $C_{18}$ column.

Formulation and Utility

The cyclic peptides disclosed herein can be used for both medical applications and animal husbandry or veterinary applications. Typically, the product is used in humans, but may also be used in other mammals. The term "patient" is intended to denote a mammalian individual, and is so used throughout the specification and in the claims. The primary applications of this invention involve human patients, but this invention may be applied to laboratory, farm, zoo, wildlife, pet, sport or other animals.

In general, the cyclic peptides of this invention may be synthesized by solid-phase synthesis and purified according to methods known in the art. Any of a number of well-known procedures utilizing a variety of resins and reagents may be used to prepare the cyclic peptides of this invention.

Salt Form of Cyclic Peptides. The cyclic peptides of this invention may be in the form of any pharmaceutically acceptable salt. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, lithium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the cyclic peptide of the present invention is basic, acid addition salts may be prepared from pharmaceutically acceptable non-toxic acids, including inorganic and organic acids. Such acids include acetic, benzenesulfonic, benzoic, camphorsulfonic, carboxylic, citric, ethanesulfonic, formic, fumaric, gluconic, glutamic, hydrobromic, hydrochloric, isethionic, lactic, maleic, malic, mandelic, methanesulfonic, malonic, mucic, nitric, pamoic, pantothenic, phosphoric, propionic, succinic, sulfuric, tartaric, p-toluenesulfonic acid, trifluoroacetic acid, and the like. Acid addition salts of the peptides of this invention are prepared in a suitable solvent from the peptide and an excess of an acid, such as hydrochloric, hydrobromic, sulfuric, phosphoric, acetic, trifluoroacetic, citric, tartaric, maleic, succinic or methanesulfonic acid. The acetate salt form is especially useful. Where the peptides of embodiments of this invention include an acidic moiety, suitable pharmaceutically acceptable salts may include alkali metal salts, such as sodium or potassium salts, or alkaline earth metal salts, such as calcium or magnesium salts.

Pharmaceutical Compositions. Another embodiment of the present invention provides a pharmaceutical composition that includes a cyclic peptide of this invention and a pharmaceutically acceptable carrier. The carrier may be a liquid formulation, and is preferably a buffered, isotonic, aqueous solution. Pharmaceutically acceptable carriers also include excipients, such as diluents, carriers and the like, and additives, such as stabilizing agents, preservatives, solubilizing agents, buffers and the like, as hereafter described.

The cyclic peptide compositions of the several embodiments of the present invention may be formulated or compounded into pharmaceutical compositions that include at least one cyclic peptide of this invention together with one or more pharmaceutically acceptable carriers, including excipients, such as diluents, carriers and the like, and additives, such as stabilizing agents, preservatives, solubilizing agents, buffers and the like, as may be desired. Formulation excipients may include polyvinylpyrrolidone, gelatin, hydroxy cellulose, acacia, polyethylene glycol, manniton, sodium chloride and sodium citrate. For injection or other liquid administration formulations, water containing at least one or more buffering constituents is preferred, and stabilizing agents, preservatives and solubilizing agents may also be employed. For solid administration formulations, any of a variety of thickening, filler, bulking and carrier additives may be employed, such as starches, sugars, fatty acids and the like. For topical administration formulations, any of a variety of creams, ointments, gels, lotions and the like may be employed. For most pharmaceutical formulations, non-active ingredients will constitute the greater part, by weight or volume, of the preparation. For pharmaceutical formulations, it is also contemplated that any of a variety of measured-release, slow-release or time-release formulations and additives may be employed, so that the dosage may be formulated so as to effect delivery of a peptide of this invention over a period of time.

In general, the actual quantity of cyclic peptides administered to a patient will vary between fairly wide ranges depending on the mode of administration, the formulation used, and the response desired.

In practical use, the cyclic peptides can be combined as the active ingredient in an admixture with a pharmaceutical carrier according to conventional pharmaceutical compounding techniques. The carrier may take a wide variety of forms depending on the form of preparation desired for administration, for example, oral, parenteral (including intravenous), urethral, vaginal, nasal, buccal, sublingual, or the like. In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, hard and soft capsules and tablets.

Because of their ease of administration, tablets and capsules represent an advantageous oral dosage unit form. If desired, tablets may be coated by standard aqueous or nonaqueous techniques. The amount of active peptide in such therapeutically useful compositions is such that an effective dosage will be obtained. In another advantageous dosage unit form, sublingual constructs may be employed, such as sheets, wafers, tablets or the like. The active peptides can also be administered intranasally as, for example, by liquid drops or spray.

The tablets, pills, capsules, and the like may also contain a binder such as gum tragacanth, acacia, corn starch or gelatin; excipients such as dicalcium phosphate; a disintegrating agent such as corn starch, potato starch or alginic acid; a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be utilized as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

Cyclic peptides may also be administered parenterally. Solutions or suspensions of these active peptides can be prepared in water suitably mixed with a surfactant such as hydroxy-propylcellulose. Dispersions can also be prepared in glycerol, liquid polyethylene glycols and mixtures thereof in oils. These preparations may optionally contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that it may be administered by syringe. The form must be stable under the conditions of manufacture and storage and must be preserved against the contaminating action of microorganisms such as bacteria and fungi. The carrier can be a solvent or dispersion medium containing, for example, water, ethanol, a polyol, for example glycerol, propylene glycol or liquid polyethylene glycol, suitable mixtures thereof, and vegetable oils.

Cyclic peptides as disclosed herein may be therapeutically applied by means of nasal administration. By "nasal administration" is meant any form of intranasal administration of any of the cyclic peptides of this invention. The peptides may be in an aqueous solution, such as a solution including saline, citrate or other common excipients or preservatives. The peptides may also be in a dry or powder formulation.

In an alternative embodiment, cyclic peptides may be administered directly into the lung. Intrapulmonary administration may be performed by means of a metered dose inhaler, a device allowing self-administration of a metered bolus of a peptide of this invention when actuated by a patient during inspiration.

According to another embodiment of the present invention, cyclic peptides of this invention may be formulated with any of a variety of agents that increase effective nasal absorption of drugs, including peptide drugs. These agents should increase nasal absorption without unacceptable damage to the mucosal membrane. U.S. Pat. Nos. 5,693,608, 5,977,070 and 5,908,825, among others, teach a number of pharmaceutical compositions that may be employed, including absorption enhancers, and the teachings of each of the foregoing, and all references and patents cited therein, are incorporated by reference.

If in an aqueous solution, certain cyclic peptides of the present invention may be appropriately buffered by means of saline, acetate, phosphate, citrate, acetate or other buffering agents, which may be at any physiologically acceptable pH, generally from about pH 4 to about pH 7. A combination of buffering agents may also be employed, such as phosphate buffered saline, a saline and acetate buffer, and the like. In the case of saline, a 0.9% saline solution may be employed. In the case of acetate, phosphate, citrate, acetate and the like, a 50 mM solution may be employed. In addition to buffering agents, a suitable preservative may be employed, to prevent or limit bacteria and other microbial growth. One such preservative that may be employed is 0.05% benzalkonium chloride.

It is also possible and contemplated that the cyclic peptide may be in a dried and particulate form. In a preferred embodiment, the particles are between about 0.5 and 6.0 µm, such that the particles have sufficient mass to settle on the lung surface, and not be exhaled, but are small enough that they are not deposited on surfaces of the air passages prior to reaching the lung. Any of a variety of different techniques may be used to make dry powder microparticles, including but not limited to micro-milling, spray drying and a quick freeze aerosol followed by lyophilization. With micro-particles, the peptides may be deposited to the deep lung, thereby providing quick and efficient absorption into the bloodstream. Further, with such approach penetration enhancers are not required, as is sometimes the case in transdermal, nasal or oral mucosal delivery routes. Any of a variety of inhalers can be employed, including propellant-based aerosols, nebulizers, single dose dry powder inhalers and multidose dry powder inhalers. Common devices in current use include metered dose inhalers, which are used to deliver medications for the treatment of asthma, chronic obstructive pulmonary disease and the like. Preferred devices include dry powder inhalers, designed to form a cloud or aerosol of fine powder with a particle size that is always less than about 6.0 µm.

Microparticle size, including mean size distribution, may be controlled by means of the method of making. For micro-milling, the size of the milling head, speed of the rotor, time of processing and the like control the microparticle size. For spray drying, the nozzle size, flow rate, dryer heat and the like control the microparticle size. For making by means of quick freeze aerosol followed by lyophilization, the nozzle size, flow rate, concentration of aerosoled solution and the like control the microparticle size. These parameters and others may be employed to control the microparticle size.

The cyclic peptides of this invention may be therapeutically administered by means of an injection, typically a deep intramuscular injection, such as in the gluteal or deltoid muscle, of a time release injectable formulation. In one embodiment, a cyclic peptide of this invention is formulated with a polyethylene glycol, such as polyethylene glycol 3350, and optionally one or more additional excipients and preservatives, including but not limited to excipients such as salts, polysorbate 80, sodium hydroxide or hydrochloric acid to adjust pH, and the like. In another embodiment a cyclic peptide of this invention is formulated with a poly(ortho ester), which may be an auto-catalyzed poly(ortho ester) with any of a variable percentage of lactic acid in the polymeric backbone, and optionally one or more additional excipients. In one embodiment poly(D,L-lactide-co-glycolide)polymer (PLGA polymer) is employed, preferably a PLGA polymer with a hydrophilic end group, such as PLGA RG502H from Boehringer Ingelheim, Inc. (Ingelheim, Germany). Such formulations may be made, for example, by combining a cyclic peptide of this invention in a suitable solvent, such as methanol, with a solution of PLGA in methylene chloride, and adding thereto a continuous phase solution of polyvinyl alcohol under suitable mixing conditions in a reactor. In general, any of a number of injectable and biodegradable polymers, which are preferably also adhesive polymers, may be employed in a time release injectable formulation. The teachings of U.S. Pat. Nos. 4,938,763, 6,432,438, and 6,673,767, and the biodegradable polymers and methods of formulation disclosed therein, are incorporated here by reference. The formulation may be such that an injection is required on a weekly, monthly or other periodic basis, depending on the concentration and amount of cyclic peptide, the biodegradation rate of the polymer, and other factors known to those of skill in the art.

Routes of Administration. If it is administered by injection, the injection may be intravenous, subcutaneous, intramuscular, intraperitoneal or other means known in the art. The peptides of this invention may be formulated by any means known in the art, including but not limited to formulation as tablets, capsules, caplets, suspensions, powders, lyophilized preparations, suppositories, ocular drops, skin patches, oral soluble formulations, sprays, aerosols and the like, and may be mixed and formulated with buffers, binders, excipients, stabilizers, anti-oxidants and other agents known in the art. In general, any route of administration by which the peptides of invention are introduced across an epidermal layer of cells may be employed. Administration means may thus include administration through mucous membranes, buccal administration, oral administration, dermal administration, inhalation administration, nasal administration, urethral administration, vaginal administration, and the like.

Therapeutically Effective Amount. In general, the actual quantity of cyclic peptide of this invention administered to a patient will vary between fairly wide ranges depending upon the mode of administration, the formulation used, and the response desired. The dosage for treatment is administration, by any of the foregoing means or any other means known in the art, of an amount sufficient to bring about the desired therapeutic effect. Thus a therapeutically effective amount includes an amount of a peptide or pharmaceutical composition of this invention that is sufficient to therapeutically alleviate feeding disorder in a patient, or to prevent or delay onset or recurrence of the feeding disorder, or for the management of the feeding disorder in patients with diseases or syndromes associated with cachexia, including secondary to immune disorders and cancer.

In general, the cyclic peptides of this invention are highly active. For example, the cyclic peptide can be administered at about 0.01, 0.05, 0.1, 0.5, 1, 5, 10, 50, 100, or 500 µg/kg body weight, depending on the specific peptide selected, the desired therapeutic response, the route of administration, the formulation and other factors known to those of skill in the art.

Inflammation and Immune-Mediated Disorders. The peptides of this invention may further be employed in the treatment of inflammation and immune-mediated disorders. See, for example, Catania A. et al., *Trends Endocrinol. Metab.* 11:304-308 (2000); Gantz I. and Fong T. M., *Am. J. Physiol. Endocrinol. Metab.* 284:E468-E474 (2003); and Catania A., Gatti S., Colombo G., Lipton J. M., *Pharmacol. Rev.* 56:1-29 (2004); each incorporated here by reference.

Combination Therapy

It is also possible and contemplated that cyclic peptides according to several embodiments of the present invention are used in combination with other drugs or agents, particularly in the treatment of cachexia. These other drugs and agents may include agents that induce weight gain, including corticosteroids and progestational agents. In a preferred embodiment of the invention, cyclic peptides of the invention are used in combination with a therapeutically effective amount of a second weight gain pharmaceutical agent.

According to another embodiment of the present invention, a method for treating cachexia is provided. The method includes administering to the patient having or at risk of having cachexia a therapeutically effective amount of a cyclic peptide as disclosed herein in combination with a therapeutically effective amount of another compound that is useful in the treatment of cachexia.

Thus one object of the present invention is to provide pharmaceutical compositions that include 1) a cyclic peptide of one embodiment of the present invention and 2) a second compound useful for the treatment of cachexia.

In an embodiment, the second compound useful for the treatment of cachexia are preferably selected from but not limited to the group consisting of ADP-ribose-polymerase inhibitors, ADP-ribose-transferase inhibitors, NADase inhibitors, nicotinamide benzamide, theophylline, thymine and analogs thereof; omega-3 fatty acids such as alpha-linolenic acid, stearidonic acid, eicosapentaenoic acid (EPA), docosapentaenoic acid, docosahexaenoic acid or mixtures thereof; branched-chain amino acids valine, leucine, isoleucine or mixtures thereof, with or without reduced levels of tryptophan and 5-hydroxytryptophan; antioxidants selected from the group comprising beta-carotene, vitamin C, vitamin E, selenium, or mixtures thereof; L-glutamine, vitamin A, vitamin C, vitamin E, and selenium; Azaftig; quinine derivatives including 3,5,6-trimethyl-2-(3-pyridyl) methyl-1,4-benzoquinone hydrochloride; interleukin 2; benzaldehyde; 4,6-O-benzylidene-D-glucose; friedelan-3-one; hydrazine sulfate; medroxyprogesterone acetate; beta 2-adrenoceptor agonists; corticosteroids such as dexamethasone; Vitor™; Pro-Stat™; megestrol acetate (Megace™); dronabinol (Marinol™); magestrol acetate (Megace™); thalidomide (Thalidomid™); fluoxymesterone (Halotestin™); pentoxifylline (Trental™); cyproheptadine (Periactin™); metoclopramide (Reglan™); total parenteral nutrition; or other MC4-R antagonists. In another embodiment, the second compound useful for the treatment of cachexia is somatropin (Serostim™), an injectable form of human growth hormone.

Another embodiment of the present invention provides kits for the treatment of cachexia. The kits include a first pharmaceutical composition including a cyclic peptide according to one embodiment of the present invention, a second pharmaceutical composition comprising a second compound useful for the treatment of cachexia, and a container for the first and second compositions.

INDUSTRIAL APPLICABILITY

The invention is further illustrated by the following non-limiting examples.

EXAMPLE 1

Competitive Inhibition Assay Using [$I^{125}$]-NDP-α-MSH

A competitive inhibition binding assay is conducted using membranes prepared using HEK-293 cells transfected with hMC3-R, hMC4-R or hMC5-R gene constructs, and B-16 mouse melanoma cells (containing MC1-R), using respectively 0.4 nM, 0.2 nM, 0.4 nM or 0.1 nM [$I^{125}$]-NDP-α-MSH (New England Nuclear) in 50 mM HEPES buffer containing 1 mM $MgCl_2$, 2 mM $CaCl_2$, and 5 mM KCl, at pH 7.2. The assay tube also contains a chosen concentration of the test peptide of this invention, typically a 1 μM concentration, for determining its efficacy in inhibiting the binding of [$I^{125}$]-NDP-α-MSH to its receptor. Non-specific binding is measured by complete inhibition of binding of [$I^{125}$]-NDP-α-MSH in the assay with the presence of 1 μM NDP-α-MSH.

The assay mixture is incubated for 90 minutes at room temperature, then filtered and the membranes washed three times with ice cold buffer. The filter is dried and counted in a gamma counter for remaining radioactivity bound to the membranes. 100% specific binding is defined as the difference in radioactivity (cpm) bound to cell membranes in the absence and presence of 1 μM NDP-α-MSH. The cpm obtained in presence of test peptides is normalized with respect to 100% specific binding to determine the percent inhibition of [$I^{125}$]-NDP-α-MSH binding. Each assay is conducted in triplicate. The Ki (nM) of certain peptides of the invention are determined using similar assay protocols and testing peptides over a wider dose range.

EXAMPLE 2

General Method for $EC_{50}$ Determination in Functional Activity Assay

Functional evaluation of peptides at melanocortin receptors is performed by measuring the accumulation of intracellular cAMP in HEK-293 cells expressing hMC3-R, hMC4-R or hMC5-R, and in B-16 mouse melanoma cells expressing MC1-R. Cells suspended in Earle's Balanced Salt Solution containing 10 mM HEPES (pH 7.5), 5 mM $MgCl_2$, 1 mM glutamine, 0.1% albumin and 0.6 mM 3-isobutyl-1-methyl-xanthine, a phosphodiesterase inhibitor, are plated in 96 well plates at a density of $0.5 \times 10^5$ cells per well. Cells are incubated with the test peptides in the presence or absence of α-MSH for 1 hour at 37° C. cAMP levels in the cell lysates are measured using the EIA kit (Amersham). Data analysis and $EC_{50}$ values are determined using nonlinear regression analysis with Prism Graph-Pad software.

EXAMPLE 3

Functional Status

The agonist/antagonist status with respect to MC1-R, MC4-R and MC5-R of certain peptides of the invention is determined. Antagonistic activity is determined by measuring the inhibition of α-MSH-induced or NDP-α-MSH-induced cAMP levels following exposure to the peptides as in the preceding descriptions.

Assay for agonist. Evaluation of the molecules to elicit a functional response in HEK-293 cells expressing hMC4-R for agonistic activity is done by measuring the accumulation of intracellular cAMP following treatment. Confluent HEK-293 cells over-expressing MC4-R are detached by enzyme free cell suspension buffer. Cells are suspended in Earle's Balanced Salt Solution containing 10 mM HEPES (pH 7.5), 1 mM $MgCl_2$, 1 mM glutamine, 0.5% albumin and 0.3 mM 3-isobutyl-1-methyl-xanthine, a phosphodiesterase inhibitor. The cells are plated in a 96 well plates at a density of $0.5 \times 10^5$ cells per well and pre-incubated for 30 minutes. The cells are then challenged with the test peptides dissolved in dimethylsulfoxide (DMSO) at a concentration range of 0.05-5000 nM in a total assay volume of 200 μL for 1 hour at 37° C. The concentration of DMSO is always held at 1% in the assay mixture. NDP-α-MSH is used as the reference agonist. At the end of the incubation period the cells are disrupted by the addition of 50 μL lysis buffer from the cAMP EIA kit (Amersham). Complete rupture of the cells is ensured by pipetting the cells up and down multiple times. cAMP levels in the cell lysates are measured after appropriate dilution using the EIA kit (Amersham) method. Data analysis and $EC_{50}$ values are determined by using nonlinear regression analysis with the Prism Graph-Pad software. Peptides at a concentration of 5000 nM with a response ratio compared to NDP-α-MSH of 0.7 and above are classified as full agonists. Peptides with a ratio from 0.1 to 0.7 are classified as partial agonists. Peptides with a response ratio of less than 0.1 are evaluated for antagonistic activity.

Assay for neutral antagonist. Peptides with a high affinity for binding to MC4-R membranes but with less efficiency ($EC_{50}$>1000 nM) and low response ratio (<0.1) are analyzed for their ability to antagonize the stimulatory effect of the agonist NDP-α-MSH. These studies are carried out in HEK-293 cells expressing hMC4-R. Cells are incubated with the peptides in the presence of the agonist NDP-α-MSH and the extent of antagonism is measured by the decrease in intracellular cAMP concentrations. Screening the peptides for antagonists is done at a single concentration of NDP-α-MSH (1.0 nM) over a peptide concentration range of 0.5-5000 nM. Studies are extended further in cases of peptides exhibiting strong antagonism to derive the $pA_2$ value from Schild's analysis.

Experimental details are similar to the analysis for agonistic activity and are described above. Briefly, cells are pre-incubated for 30 minutes with the test peptides at concentrations between 0.5 nM and 5000 nM. The cells are then stimulated with NDP-α-MSH at a concentration of 1 nM for 1 hour. For Schild's analysis, the interactions are studied using at least 3 concentrations of the peptides, separated by a log unit, over a full range of the agonist (0.005-5000 nM). cAMP levels is measured in the cell lysates after appropriate dilution. Nonlinear regression analysis with the Prism Graph-Pad software is used for Schild's analysis and to obtain $EC_{50}$ values. $pA_2$ values are derived from the Schild's plot.

Assay for inverse agonist. Peptides that have a weak $EC_{50}$ value ($EC_{50}$>1000 nM) or a low response ratio (<0.1) are also investigated for their ability to act as inverse agonists, i.e. to decrease the basal or constitutive level of cAMP in HEK-293 cells expressing hMC4-R receptors. The experimental protocol is essentially the same a described above. The cells are exposed to the test peptides over a concentration range of 0.05 nM to 5000 nM for 1 hour at 37° C. Agouti-related protein (AgRP) or a biologically active fragment of Agouti protein, such as AgRP (83-132) (Ser-Ser-Arg-Arg-Cys-Val-Arg-Leu-His-Glu-Ser-Cys-Leu-Gly-Gln-Gln-Val-Pro-Cys-Cys-Asp-Pro-Cys-Ala-Thr-Cys-Tyr-Cys-Arg-Phe-Phe-Asn-Ala-Phe-Cys-Tyr-Cys-Arg-Lys-Leu-Gly-Thr-Ala-Met-Asn-Pro-Cys-Ser-Arg-Thr (SEQ ID NO:2)) is used as the reference inverse agonist. Data analysis and $EC_{50}$ values are determined by using nonlinear regression analysis with the Prism Graph-Pad software.

EXAMPLE 4

ICV Food Intake and Body Weight Change

Change in food intake and body weight is evaluated for selected peptides. Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed ICV with vehicle or selected cyclic peptides (0.3-3 nmol). The changes in body weight and food intake for the 24 hour period after dosing are determined. The changes in body weight and food intake for the 48 hour and 72 hour periods after dosing are also measured to determine reversal of changes in body weight and food intake effects back to baseline levels.

EXAMPLE 5

IV and IP Food Intake and Body Weight Change

Change in food intake and body weight is evaluated for selected peptides. Male Sprague-Dawley rats are obtained from Taconic (Germantown, N.Y.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food is provided ad libitum. For 1 week before treatment, 24-hour food intake and body weight change is recorded to assess a baseline for the group during vehicle treatment. The rats are dosed IV or IP with vehicle or selected peptides (0.5-3 mg/kg). The changes in body weight and food intake for the 24 hour period after dosing are determined. The changes in body weight and food intake for the 48 hour and 72 hour periods after dosing are also measured to determined reversal of changes in body weight and food intake effects back to baseline levels.

EXAMPLE 6

Behavioral Satiety Sequence

Male Sprague-Dawley rats are maintained on a restricted diet of 20 g powdered food per day. Food is presented at the same time during the lights-on period, dosed with either saline or the test peptide 2 hours before presentation of food and the start of observation. Pre-weighed bowls containing 20 g of food are presented and the behavior of the rats is observed for 1 hour. Behavioral observations are divided into 3 categories: Feeding, Active (includes grooming, drinking and sniffing/exploration), and Resting (decreased activity and sleep). The amount of time spent in each behavior is recorded. The amount of food intake is determined after the observation period.

EXAMPLE 7

Conditioned Taste Avoidance

Male Sprague-Dawley rats are adapted to a restricted drinking period of 30 minutes per day during lights on and are provided with pelleted chow ad libitum. In laboratory animals the administration of LiCl conditions an aversion to the novel and favorable taste of saccharin (Seeley R. J., Blake K., Rushing P. A. et al. The role of CNS glucagons-like peptide-1 (7-36) amide receptors in mediating the visceral illness effects of lithium chloride. *J. Neurosci.* 20:1616-1621 (2000)). To condition animals, an injection of LiCl or test peptide is administered immediately after the initial presentation of a 0.1% solution of saccharin. Two days later, saccharin solution is again presented and fluid intake determined. A decrease in drinking the saccharin solution suggests development of a conditioned taste aversion.

EXAMPLE 8

Lipopolysaccharide-Induced Cachexia Model

Rats with indwelling intracerebroventricular cannulas (ICV rats) are obtained from Hilltop Lab Animals, Inc. (Scottdale, Pa.). Animals are individually housed in conventional plexiglass hanging cages and maintained on a controlled 12 hour on/off light cycle. Water and powdered (LabDiet, 5P00 Prolab RMH 3000) or pelleted (Harlan Teklad 2018 18% Protein Rodent Diet) food are provided ad libitum. Lipopolysaccharide (LPS) (*E. Coli* 055:B5, Sigma Chemical Co.) is dissolved in normal saline and administered i.p. For the first LPS injection, male animals aged 6-7 weeks are used. In an identical repeat experiment, female animals, aged 5 weeks are used. Animals have basal feeding monitored for two days, and then during each twelve hour period following an i.p. saline injection prior to injection of 100 μg/kg of LPS. Certain peptides of the invention are administered, and 50 μg/kg LPS are administered 3 hours later. A second dose of 100 μg/Kg LPS is given 60 hours after the first dose in the second experiment. No food is available between peptide administration and LPS administration. Starting after LPS administration, feeding is measured every 6 hours for 24 hours, then every 12 hours for 48 more hours.

In the sham group, basal feeding is measured every six hours in two age and sex-matched groups after simulated ICV injection and i.p. saline injection. Twenty-four hours later, selected peptides are administered, and LPS is administered i.p. 3 hours later. Feeding is measured every 6 hours for 24 hours, then every 12 hours for 48 more hours. The difference between feeding curves in the two groups is expressed both as weight normalized intake and as a percent of basal feeding vs. post-saline and sham ICV injection.

EXAMPLE 9

Tumor-induced Cachexia Model

Lewis lung carcinoma (LLC) cells and Englebreth-Holm-Swarm Sarcoma (EHS) tumors are maintained either as a primary culture in DMEM with 10% fetal bovine serum or in vivo, respectively, as recommended by the supplier. LLC tumor cells are harvested during exponential growth of the culture, washed in Hanks balanced salt solution, and cells are injected subcutaneously into the upper flank of the animals. EHS sarcoma tissue is dissected from a donor animal, and an approximately 3 mm cube of tissue is implanted subcutaneously above the rear flank. Sham operated animals receive an implant of a similar amount of donor muscle tissue. In all cases, the time of appearance of a tumor mass is noted, and all animals are found to have a palpable tumor within four (LLC) or eight (EHS) days of the start of the experiment. At the time of sacrifice, tumors are dissected away from surrounding tissue and weighed. Gross examination of all organs does not reveal the presence of any observable metastasis. Trunk blood is collected at the time of sacrifice for measurement of serum leptin with a rat leptin radioimmunoassay kit.

Animals are individually housed in conventional plexiglass hanging cages and maintained on a controlled 12 hour on/off light cycle. The effects of administration of certain peptides of the invention in animals with hypophagia and weight loss due to the presence of a growing sarcoma are examined. In an initial experiment, daily food intake and weight are followed until the tumor-bearing animals have food intake that is 75-80% of basal for three consecutive days. On average this occurs on day 12 post-implant, or four days after a palpable tumor is present. ICV injection of the selected peptides is performed and animals are monitored to assess the change in food intake.

In a second experiment the ability of selected peptides to prevent the onset of cachexia and maintain normal feeding and growth is tested. Animals are examined daily for the presence of a palpable tumor, with all animals having tumors by day 14 post implantation, and none prior to day 12. Animals are then injected with selected peptides or a sham every 48 hours until sacrifice. A sham-tumor implanted group is included for comparison and is also given the peptides.

Differences between feeding, activity, and water consumption curves in all experiments are analyzed by two-way, repeated measure ANOVA with time and treatment as the measured variables. Final tumor and body weights are analyzed by Student's t-test when two groups are included, or one way ANOVA with post-hoc analysis when three groups are included. Data sets are analyzed for statistical significance using either the PRISM software package (GraphPad) for ANOVA with repeated measures, or in EXCEL (Microsoft) using Student's t-test.

EXAMPLE 10

Determination of Mass and Nuclear Magnetic Resonance Analysis

The mass values of peptides of the invention are determined using a Waters MicroMass ZQ device utilizing a positive mode. Mass determinations are compared with calculated values and expressed in the form of mass weight plus one (M+1 or M+H).

Proton NMR data is obtained using a Bruker 300 MHz spectrometer. The spectra are obtained after dissolving peptides in a deuteriated solvent such as chloroform, DMSO, or methanol as appropriate.

EXAMPLE 11

Ac-Nle-cyclo(-Asp-His-D-Nal 2-Arg-Trp-Lys)-OH

The peptide Ac-Nle-cyclo(-Asp-His-D-Nal 2-Arg-Trp-Lys)-OH was synthesized by conventional peptide synthesis methods. The formula weight was determined to be 1189. Competitive inhibition testing and Ki (nM) of the peptide was measured following the method of Example 1. Functional status of the peptide was determined following the methods of Examples 2 and 3.

| Ki (nM) | | | |
|---|---|---|---|
| MC1-R | MC3-R | MC4-R | MC5-R |
| 3 | 10 | 0.6 | 3 |

In a cAMP assay for determination of agonist/antagonist status, it was determined that the peptide was a partial agonist as to MC1-R with an $EC_{50}$ (nm) of 57, and was an antagonist as to MC3-R and MC4-R. In tests for functional antagonism as in Example 3, a pA$_2$ (M) value as to MC4-R of 7.95 was determined.

EXAMPLE 12

Ac-Nle-cyclo(-Asp-His-D-Nal 2-Arg-Nal 2-Lys)-OH

The peptide Ac-Nle-cyclo(-Asp-His-D-Nal 2-Arg-Nal 2-Lys)-OH was synthesized by conventional peptide synthesis methods. The formula weight was determined to be 1200. Competitive inhibition testing and Ki (nM) of the peptide was measured following the method of Example 1. Functional status of the peptide was determined following the methods of Examples 2 and 3.

| Ki (nM) | | | |
|---|---|---|---|
| MC1-R | MC3-R | MC4-R | MC5-R |
| 0.2 | 0.3 | 0.02 | 0.2 |

In a cAMP assay for determination of agonist/antagonist status, it was determined that the peptide was a partial agonist as to MC1-R with an EC$_{50}$ (nm) of 5, and was an antagonist as to MC3-R and MC4-R. In tests for functional antagonism as in Example 3, a pA$_2$ (M) value as to MC4-R of 8.12 was determined.

Figure 2:
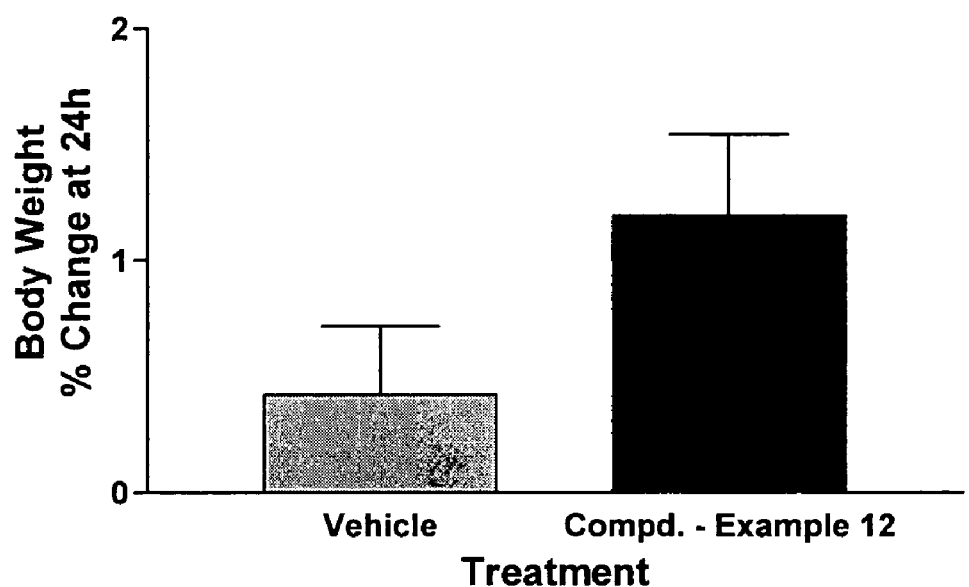
FIG. 2 is a graph of the change in body weight at 24 hours in the animals of FIG. 1.

FIG. 1 illustrates the cumulative increase in food intake, in grams, in rats administered the compound of Example 12 compared to vehicle alone. Rats were administered 1 mg/kg of the peptide of Example 12 as in Example 5, and food intake was measured at selected times for a 24 hour period. Briefly, male Sprague-Dawley rats (300-350 g) were individually housed in shoe box cages with a 12 hr light/dark period. Food intake and body weights were monitored for 24 hours prior to the start of the study. Rats were randomized by body weight and then dosed IV just before lights-off with the compound of Example 12 or the same volume of vehicle. A pre-weighed amount of food was provided and food intake was determined at 2, 4, 20 and 24 hours. In FIG. 1, "*" indicates a probability of p<0.05, and "**" indicates a probability of p<0.01. FIG. 2 shows the cumulative change in body weight for the animals of FIG. 1 at 24 hours.

EXAMPLE 13

Ac-Nle-cyclo(-Asp-Trp-D-Nal 2-Arg-Nal 2-Lys)-OH

The peptide Ac-Nle-cyclo(-Asp-Trp-D-Nal 2-Arg-Nal 2-Lys)-OH was synthesized by conventional peptide synthesis methods. The formula weight was determined to be 1249. Competitive inhibition testing and Ki (nM) of the peptide was measured following the method of Example 1. Functional status of the peptide was determined following the methods of Examples 2 and 3.

| Ki (nM) | | | |
|---|---|---|---|
| MC1-R | MC3-R | MC4-R | MC5-R |
| 119 | 4 | 0.2 | 0.9 |

In a cAMP assay for determination of agonist/antagonist status, it was determined that the peptide was a partial agonist as to MC1-R and an antagonist as to MC3-R and MC4-R. In tests for functional antagonism as in Example 3, a pA$_2$ (M) value as to MC4-R of 7.59 was determined.

EXAMPLE 14

Ac-cyclo(-Asp-His-D-Nal 2-Arg-Trp-Lys)-OH

The peptide Ac-cyclo(-Asp-His-D-Nal 2-Arg-Trp-Lys)-OH was synthesized by conventional peptide synthesis methods. The formula weight was determined to be 1076. Competitive inhibition testing and Ki (nM) of the peptide was measured following the method of Example 1. Functional status of the peptide was determined following the methods of Examples 2 and 3.

| Ki (nM) | | | |
|---|---|---|---|
| MC1-R | MC3-R | MC4-R | MC5-R |
| 181 | 55 | 2 | 191 |

In a cAMP assay for determination of agonist/antagonist status, it was determined that the peptide was an agonist as to MC1-R with an EC$_{50}$ (nm) of 4420, and was an antagonist as to MC3-R and MC4-R, with an EC$_{50}$ (nm) as to MC3-R of 1.0. In tests for functional antagonism as in Example 3, a pA$_2$ (M) value as to MC4-R of 6.73 was determined.

EXAMPLE 15

Ac-cyclo(-Asp-His-D-Nal 2-Arg-Nal 2-Lys)-OH

The peptide Ac-cyclo(-Asp-His-D-Nal 2-Arg-Nal 2-Lys)-OH was synthesized by conventional peptide synthesis methods. The formula weight was determined to be 1088. Competitive inhibition testing and Ki (nM) of the peptide was measured following the method of Example 1. Functional status of the peptide was determined following the methods of Examples 2 and 3.

| Ki (nM) | | | |
|---|---|---|---|
| MC1-R | MC3-R | MC4-R | MC5-R |
| 143 | 6 | 2 | 89 |

In a cAMP assay for determination of agonist/antagonist status, it was determined that the peptide was a partial agonist as to MC1-R with an EC$_{50}$ (nm) of 2153, and was an antagonist as to MC3-R and MC4-R. In tests for functional antagonism as in Example 3, a pA$_2$ (M) value as to MC4-R of 8.0 was determined.

EXAMPLE 16

Ac-cyclo(-Asp-Trp-D-Nal 2-Arg-Nal 2-Lys)-OH

The peptide Ac-cyclo(-Asp-Trp-D-Nal 2-Arg-Nal 2-Lys)-OH was synthesized by conventional peptide synthesis methods. The formula weight was determined to be 1137. Competitive inhibition testing and Ki (nM) of the peptide was measured following the method of Example 1. Functional status of the peptide was determined following the methods of Examples 2 and 3.

| Ki (nM) | | | |
| --- | --- | --- | --- |
| MC1-R | MC3-R | MC4-R | MC5-R |
| 1098 | 10 | 0.1 | 17 |

In a cAMP assay for determination of agonist/antagonist status, it was determined that the peptide was a partial agonist as to MC1-R with an $EC_{50}$ (nm) of >1000 and an antagonist as to MC3-R and MC4-R. In tests for functional antagonism as in Example 3, a $pA_2$ (M) value as to MC4-R of 8.45 was determined.

EXAMPLE 17

Ac-cyclo(-Asp-Trp-D-Nal 2-Arg-Nal 2-Lys)-NH—CH$_2$—CH$_3$

The peptide Ac-cyclo(-Asp-Trp-D-Nal 2-Arg-Nal 2-Lys)-NH—CH$_2$—CH$_3$ was synthesized by conventional peptide synthesis methods. The formula weight was determined to be 1163. Competitive inhibition testing and Ki (nM) of the peptide was measured following the method of Example 1. Functional status of the peptide was determined following the methods of Examples 2 and 3.

| Ki (nM) | | | |
| --- | --- | --- | --- |
| MC1-R | MC3-R | MC4-R | MC5-R |
| 194 | 1 | 0.03 | 3 |

In a cAMP assay for determination of agonist/antagonist status, it was determined that the peptide was a partial agonist as to MC1-R with an $EC_{50}$ (nm) of >1000 and an antagonist as to MC3-R and MC4-R. In tests for functional antagonism as in Example 3, a $pA_2$ (M) value as to MC4-R of 8.76 and $pA_2$ (M) value as to MC3-R of 8.04 was determined.

EXAMPLE 18

Ac-cyclo(-Asp-Trp-D-Nal 2-Arg-Nal 2-Lys)-N(CH$_3$)$_2$

The peptide Ac-cyclo(-Asp-Trp-D-Nal 2-Arg-Nal 2-Lys)-N(CH$_3$)$_2$ was synthesized by conventional peptide synthesis methods. The formula weight was determined to be 1163. Competitive inhibition testing and Ki (nM) of the peptide was measured following the method of Example 1. Functional status of the peptide was determined following the methods of Examples 2 and 3.

| Ki (nM) | | | |
| --- | --- | --- | --- |
| MC1-R | MC3-R | MC4-R | MC5-R |
| 107 | 1 | 0.03 | 4 |

In a cAMP assay for determination of agonist/antagonist status, it was determined that the peptide was inactive as to MC1-R and an antagonist as to MC3-R and MC4-R. In tests for functional antagonism as in Example 3, a $pA_2$ (M) value as to MC4-R of 8.69 and $pA_2$ (M) value as to MC3-R of 7.29 was determined.

EXAMPLE 19

Ac-cyclo(-Asp-Trp-D-Nal 2-Arg-Nal 2-Lys)-NH—CH$_3$

The peptide Ac-cyclo(-Asp-Trp-D-Nal 2-Arg-Nal 2-Lys)-NH—CH$_3$ was synthesized by conventional peptide synthesis methods. The formula weight was determined to be 1149. Competitive inhibition testing and Ki (nM) of the peptide was measured following the method of Example 1. Functional status of the peptide was determined following the methods of Examples 2 and 3.

| Ki (nM) | | | |
| --- | --- | --- | --- |
| MC1-R | MC3-R | MC4-R | MC5-R |
| 643 | 3 | 0.06 | 6 |

In a cAMP assay for determination of agonist/antagonist status, it was determined that the peptide at 1 µM concentration was inactive at MC1-R, and an antagonist as to MC3-R and MC4-R. In tests for functional antagonism as in Example 3, a $pA_2$ (M) value as to MC4-R of 8.9 and $pA_2$ (M) value as to MC3-R of 8.07 was determined.

EXAMPLE 20-25

Additional Peptides

The following peptides were synthesized by conventional peptide synthesis methods:

20. H-cyclo(-Asp-Trp-D-Nal 2-Arg-Nal 2-Lys)-NH—CH$_2$—CH$_3$
21. H-cyclo(-Asp-Trp-D-Nal 2-Arg-Nal 2-Lys)-NH—CH$_3$
22. H-cyclo(-Asp-Trp-D-Nal 2-Arg-Nal 2-Lys)-N(CH$_3$)$_2$
23. H-cyclo(-Asp-Trp-D-Nal 2-Lys-Nal 2-Lys)-NH—CH$_2$—CH$_3$
24. H-cyclo(-Asp-Trp-D-Nal 2-Lys-Nal 2-Lys)-NH—CH$_3$
25. H-cyclo(-Asp-Trp-D-Nal 2-Lys-Nal 2-Lys)-N(CH$_3$)$_2$ Competitive inhibition and Ki (nM) of the peptides of Examples 20-25 are measured following the method of Example 1. Functional status of the peptides of Examples 20-25 are determined following the methods of Examples 2 and 3.

EXAMPLE 26

ICV Feeding Studies

A series of ICV feeding studies were conducted on rats. All animals were dosed on the first day with saline ICV, and given a pre-weighed food bowl with food weight recorded at 2 and 21 hours post-ICV injection. On day 2, animals were randomized based on the 21 hour food consumption, with animals eliminated due to low food consumption or food spills. Animals were dosed with vehicle (saline), a positive control (SHU9119 at 1 nmol) or peptides of the invention (at 0.3 or 3 nmol). Food weights were again recorded at 2, 4, 21 and 24 hours post-icv injection. In most instances, multiple different tests were conducted which each group containing between 8 and 12 members; the lowest value is shown below. Values are shown as percent increase (decrease) in aggregate food intake. "ND" means no test was conducted at that dose level.

| Peptide of: | Percent Increase (Decrease) In Aggregate Food Intake After ICV Administration of Peptide Compared to Vehicle (Saline) | |
|---|---|---|
| | 0.3 nmol | 1 nmol |
| Example 11 | ND | 24% |
| Example 12 | 36% | 48% |
| Example 13 | ND | (4)% |
| Example 14 | ND | 16% |
| Example 15 | ND | 32% |
| Example 16 | 0% | 4% |
| Example 17 | 32% | 20% |
| Example 18 | 24% | 24% |
| Example 19 | 28% | 32% |

The preceding examples can be repeated with similar success by substituting the generically or specifically described reactants and/or operating conditions of this invention for those used in the preceding examples.

Although the invention has been described in detail with particular reference to these preferred embodiments, other embodiments can achieve the same results. Variations and modifications of the present invention will be obvious to those skilled in the art and it is intended to cover all such modifications and equivalents. The entire disclosures of all references, applications, patents, and publications cited above are hereby incorporated by reference.

What is claimed is:

1. A synthetic cyclic peptide of the structural formula:

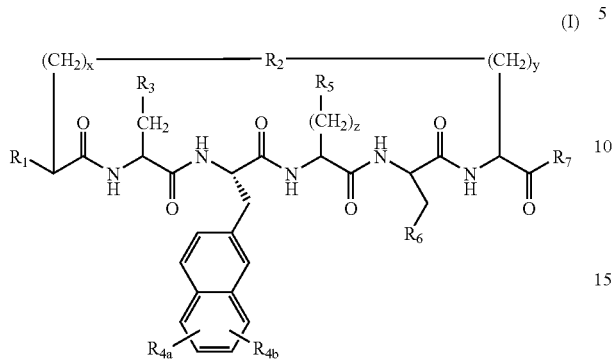

(I)

wherein:

$R_1$ is H, $NH_2$, or

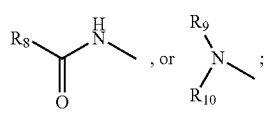

$R_2$ is —C(=O)—NH— or —NH—C(=O)—;

$R_3$ is 4-imidazolyl or 3-indolyl;

$R_{4a}$ and $R_{4b}$ are each optional ring substituents, and when one or both are present, are the same or different and independently hydroxyl, halogen, alkyl, or aryl groups attached directly or through an ether linkage;

$R_5$ is —$NH_2$ or —NH(C=NH)$NH_2$;

$R_6$ is 1- or 2-naphthyl or 3-indolyl, optionally with one or two ring substituents, and when one or both ring substituents are present, are the same or different and independently hydroxyl, halogen, alkyl, or aryl groups attached directly or through an ether linkage;

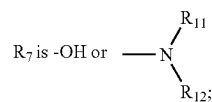

$R_7$ is -OH or $R_8$ is H, $NH_2$, a lower aliphatic $C_1$ to $C_4$ linear or branched alkyl chain, a $C_1$ to $C_4$ aralkyl, or a $C_1$ to $C_4$ aliphatic moiety with a terminal amino group;

$R_9$ is H, a lower aliphatic $C_1$ to $C_4$ linear or branched alkyl chain, a $C_1$ to $C_4$ aralkyl, or a $C_1$ to $C_4$ aliphatic moiety with a terminal amino group;

$R_{10}$ is an aliphatic L- or D-amino acid, an N-acylated L- or D-amino acid or a linear or branched $C_1$ to $C_{17}$ alkyl, aryl, heteroaryl, alkene, alkenyl, or aralkyl chain;

$R_{11}$ and $R_{12}$ are each independently H or a $C_1$ to $C_4$ linear or brarfched alkyl chain, on the proviso that both $R_{11}$ and $R_{12}$ are not H;

x is 1 to 4, and y is 1 to 5, provided that x+y is 2 to 7; and z is 2 to 5.

2. The cyclic peptide of claim 1 of the structural formula:

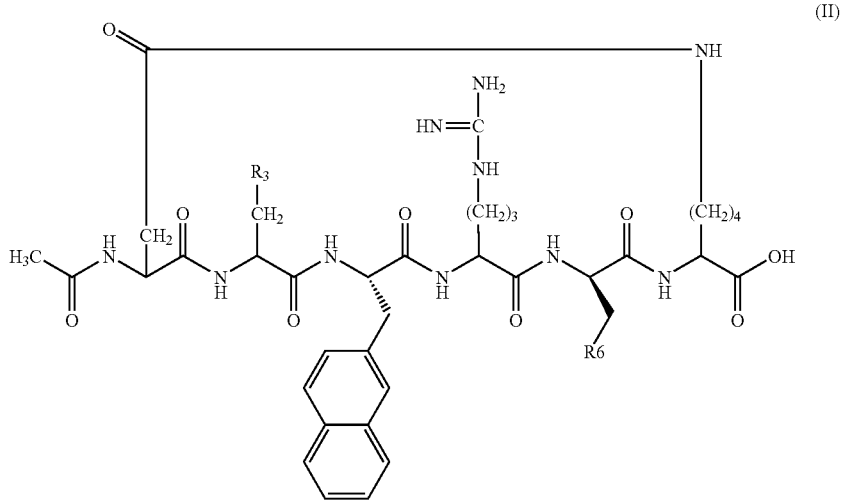

(II)

wherein $R_3$ and $R_6$ are as defined in claim 1.

3. The cyclic peptide of claim 2 which is:

Ac-cyc/o(-Asp-His-D-Nal 2-Arg-Trp-Lys)-OH;
Ac-cyc/o(-Asp-His-D-Nal 2-Arg-Nal 2-Lys)-OH; or
Ac-cyc/o(-Asp-Trp-D-Nal 2-Arg-Nal 2-Lys)-OH.

4. The cyclic peptide of claim 1 of the structural formula:

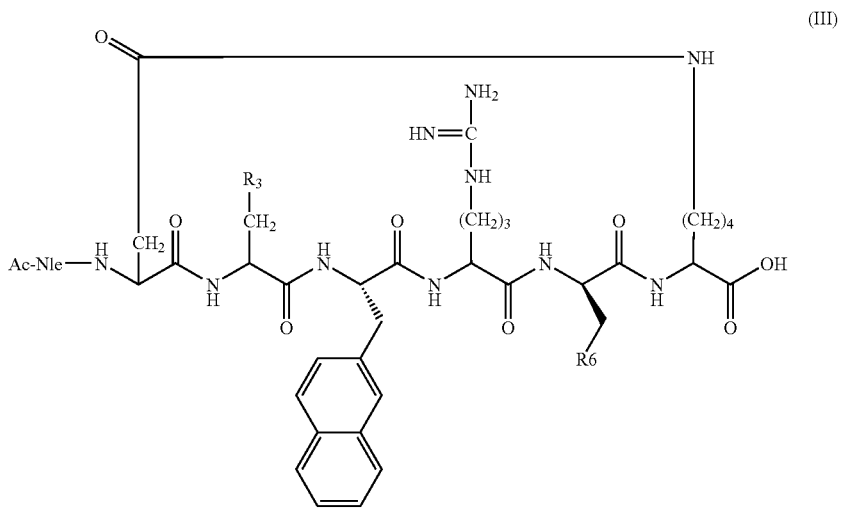

(III)

wherein $R_3$ and $R_6$ are as defined in claim 1.

5. The cyclic peptide of claim 4 which is:
Ac-Nle-cyc/o(-Asp-His-D-Nal 2-Arg-Trp-Lys)-OH;
Ac-Nle-cyc/o(-Asp-His-D-Nal 2-Arg-Nal 2-Lys)-OH; or
Ac-Nle-cyc/o(-Asp-Trp-D-Nal 2-Arg-Nal 2-Lys)-OH.

6. The cyclic peptide of claim 1 of the structural formula:

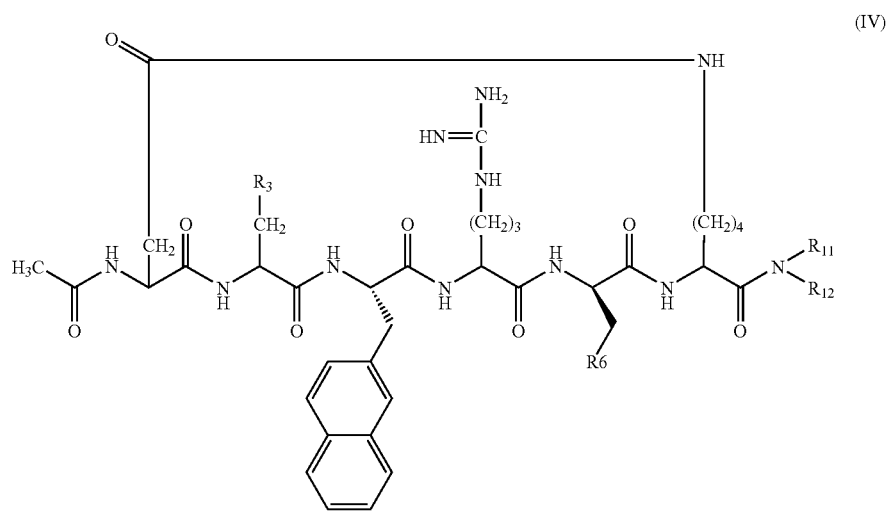

(IV)

wherein $R_3$, $R_6$, $R_{11}$ and $R_{12}$ are as defined in claim 1.

7. The cyclic peptide of claim 6 which is:
Ac-cyclo(-Asp-Trp-D-Nal 2-Arg-Nal 2-Lys)-NH—CH$_2$—CH$_3$;
Ac-cyclo(-Asp-Trp-D-Nal 2-Arg-Nal 2-Lys)-N(CH$_3$)$_2$; or
Ac-cyclo(-Asp-Trp-D-Nal 2-Arg-Nal 2-Lys)-NH—CH$_3$.

8. The cyclic peptide of claim 1 of the structural formula:

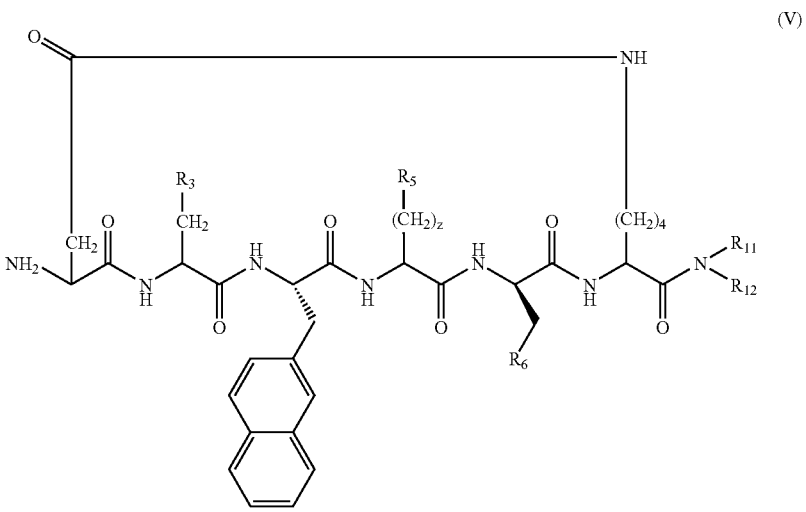

(V)

wherein $R_3$, $R_5$, $R_6$, $R_{11}$, $R_{12}$ and z are as defined in claim 1.

9. The cyclic peptide of claim 8 which is:
H-cyclo(-Asp-Trp-D-Nal 2-Arg-Nal 2-Lys)-NH—$CH_2$—$CH_3$;
H-cyclo(-Asp-Trp-D-Nal 2-Arg-Nal 2-Lys)-NH—$CH_3$;
H-cyclo(-Asp-Trp-D-Nal 2-Arg-Nal 2-Lys)-N($CH_3$)$_2$;
H-cyclo(-Asp-Trp-D-Nal 2-Lys-Nal 2-Lys)-NH—$CH_2$—$CH_3$;
H-cyclo(-Asp-Trp-D-Nal 2-Lys-Nal 2-Lys)-NH—$CH_3$; or
H-cyclo(-Asp-Trp-D-Nal 2-Lys-Nal 2-Lys)-N($CH_3$)$_2$.

10. A pharmaceutical preparation, comprising a cyclic peptide of claim 1 or a pharmaceutically acceptable salt thereof, and a pharmaceutically acceptable carrier.

11. A method of treating cachexia, comprising administering a pharmaceutically sufficient amount of a pharmaceutical preparation of claim 10 to a mammal, wherein the amount of the pharmaceutical preparation is effective to alleviate the symptom of cachexia.

12. A synthetic cyclic hexapeptide with a C-terminus hydroxyl or N-alkyl group, wherein the N-alkyl group comprises one or two $C_1$ to $C_4$ linear or branched alkyl chains, the hexapeptide containing the core sequence His-D-Nal 2-X—Y or Trp-D-Nal 2-X—Y in positions 2 through 5, wherein X is an L-amino acid residue selected from the group consisting of Arg, Lys, Orn, Harg and Hlys and Y is an L- or D-amino acid residue selected from the group consisting of Nal 1, Nal 2 Trp, wherein any aromatic ring in the core sequence optionally includes one or two ring substituents, and when one or both ring substituents are present, are the same or different and independently hydroxyl, halogen, alkyl, or aryl groups attached directly or through an ether linkage, and wherein the cyclic hexapeptide is cyclized through the amino acid residue in the 1 position and the amino acid residue in the 6 position by formation of a covalent amide bond.

13. The cyclic hexapeptide of claim 12 with an N-terminus Ac group.

14. The cyclic hexapeptide of claim 12 wherein the hexapeptide is cyclized by formation of an amide bond between an amino group of a side chain of an amino acid in the 1 position or an amino group of the N-terminus group of the amino acid in the 1 position and a side chain carboxyl group of an amino acid residue at the 6 position.

15. The cyclic hexapeptide of claim 12, wherein the hexapeptide is cyclized by formation of an amide bond between a side chain carboxyl group of an amino acid residue in the 1 position and an amino group of a side chain of an amino acid at the 6 position.

16. The cyclic hexapeptide of claim 12 wherein the core sequence is His-D-Nal 2-X-Nal 2.

17. The cyclic hexapeptide of claim 12 wherein the core sequence is Trp-D-Nal 2-X-Nal 2.

18. The cyclic hexapeptide of claim 12 wherein the core sequence is His-D-Nal 2-X-Trp.

* * * * *

UNITED STATES PATENT AND TRADEMARK OFFICE
CERTIFICATE OF CORRECTION

| | |
|---|---|
| PATENT NO. | : 7,342,089 B2 |
| APPLICATION NO. | : 11/174845 |
| DATED | : March 11, 2008 |
| INVENTOR(S) | : Sharma et al. |

It is certified that error appears in the above-identified patent and that said Letters Patent is hereby corrected as shown below:

On the Title page item (54) and col. 1, line 1,
In the Title, delete the second occurrence of word "FOR" and replace with the word --OF--, such that the title reads --Cyclic Peptides for Treatment of Cachexia--.

Column 35, line 22, delete the word "or".

Column 36, line 26 replace the word "brarfched" with --branched--; lines 65-67, replace the word "cyc/o" with --cyclo--.

Columns 37 - 38, lines 25-28, replace the word "cyc/o" with --cyclo--.

Column 39, line 50, replace the word "Om" with --Orn--; and line 52, replace "Nal 2 Trp" with --Nal 2 and Trp--.

Signed and Sealed this

Seventeenth Day of June, 2008

JON W. DUDAS
*Director of the United States Patent and Trademark Office*

UNITED STATES PATENT AND TRADEMARK OFFICE
CERTIFICATE OF CORRECTION

PATENT NO.         : 7,342,089 B2                                          Page 1 of 1
APPLICATION NO. : 11/174845
DATED              : July 5, 2005
INVENTOR(S)        : Sharma et al.

It is certified that error appears in the above-identified patent and that said Letters Patent is hereby corrected as shown below:

On the initial cover page of the patent, under the heading "Related U.S. Application Data" and after paragraph numbered "(63)", insert the following paragraph:

--(60)  Provisional application No. 60/585,971, filed on Jul. 6, 2004.--

In column 1, after the first paragraph beginning at line 7 but before the heading "BACKGROUND OF THE INVENTION" insert the following paragraph:

--This application claims priority to and the benefit of the filing of U.S. Provisional Patent Application Ser. No. 60/585,971, entitled "Cyclic Peptides for Treatment of Cachexia", filed on Jul. 6, 2004, and the specification and proposed claims thereof are incorporated herein by reference.--

Signed and Sealed this

Eleventh Day of August, 2009

David J. Kappos
*Director of the United States Patent and Trademark Office*